(12) United States Patent
Ivri

(10) Patent No.: US 9,108,211 B2
(45) Date of Patent: Aug. 18, 2015

(54) VIBRATION SYSTEMS AND METHODS

(75) Inventor: Yehuda Ivri, Newport Beach, CA (US)

(73) Assignee: Nektar Therapeutics, San Francisco, CA (US)

( * ) Notice: Subject to any disclaimer, the term of this patent is extended or adjusted under 35 U.S.C. 154(b) by 2365 days.

(21) Appl. No.: 11/920,805

(22) PCT Filed: Apr. 17, 2006

(86) PCT No.: PCT/US2006/014654
§ 371 (c)(1),
(2), (4) Date: Nov. 19, 2007

(87) PCT Pub. No.: WO2006/127181
PCT Pub. Date: Nov. 30, 2006

(65) Prior Publication Data
US 2009/0134235 A1    May 28, 2009

Related U.S. Application Data

(60) Provisional application No. 60/684,720, filed on May 25, 2005.

(51) Int. Cl.
*A61M 15/00* (2006.01)
*A61M 16/00* (2006.01)
(Continued)

(52) U.S. Cl.
CPC ............ *B05B 17/0676* (2013.01); *A61M 15/00* (2013.01); *A61M 15/009* (2013.01);
(Continued)

(58) Field of Classification Search
CPC .......... B05B 1/00; B05B 17/00; B05B 17/04; B05B 17/06; B05B 17/0607; B05B 17/0638; B05B 17/0646; A61M 15/00; A61M 15/009

USPC ............ 128/200.13, 200.16, 200.14, 200.15, 128/200.17, 200.18, 203.12, 203.15, 128/203.19; 73/662, 663, 668, 721, 727; 374/117, 118; 239/4, 102.1, 102.2
See application file for complete search history.

(56) References Cited

U.S. PATENT DOCUMENTS 550,315 A    11/1895  Allen
809,159 A    1/1906   Willis et al.
(Continued)

FOREIGN PATENT DOCUMENTS

DE    11 03 522    3/1961
DE    3513628      10/1986
(Continued)

OTHER PUBLICATIONS

PCT ISR App No. PCT/US06/14654, mail date Nov. 19, 2007, Intl Filing date Apr. 17, 2006.
(Continued)

*Primary Examiner* — Victoria J Hicks
*Assistant Examiner* — Brandon L Jackson
(74) *Attorney, Agent, or Firm* — Kilpatrick Townsend & Stockton LLP

(57) ABSTRACT

In one arrangement, a vibration system includes a vibratable plate, a support member surrounding the vibratable plate, and a vibration-inducing member surrounding the support member. The vibration-inducing member is configured to radially expand and contract against the support member so as to produce axial vibration of the vibratable plate. In another arrangement, the vibratable plate has an outer circumference; a tubular member is concentrically disposed about the outer circumference of the plate, and an annular vibration-inducing member is concentrically disposed about the outer circumference of the tubular member. The vibration-inducing member is preferably a piezoelectric ring that is radially expandable and contractable against the wall of the tubular member to cause the plate to vibrate in the axial direction.

38 Claims, 11 Drawing Sheets

(51) Int. Cl.

| | | |
|---|---|---|
| *A61M 11/00* | (2006.01) | |
| *B05B 17/06* | (2006.01) | |
| *B05B 3/02* | (2006.01) | |
| *B05B 1/26* | (2006.01) | |
| *B05B 17/04* | (2006.01) | |
| *B05B 1/08* | (2006.01) | |
| *B05B 3/04* | (2006.01) | |
| *B05B 1/00* | (2006.01) | |
| *B05B 17/00* | (2006.01) | |

(52) U.S. Cl.
CPC ................. *B05B 1/00* (2013.01); *B05B 17/00* (2013.01); *B05B 17/04* (2013.01); *B05B 17/06* (2013.01); *B05B 17/0638* (2013.01); *B05B 17/0646* (2013.01); *Y10T 29/42* (2015.01)

(56) References Cited

U.S. PATENT DOCUMENTS

| | | | |
|---|---|---|---|
| 1,680,616 A | 8/1928 | Horst | |
| 2,022,520 A | 11/1935 | Philbrick | |
| 2,101,304 A | 12/1937 | Wright | |
| 2,158,615 A | 5/1939 | Wright | |
| 2,187,528 A | 1/1940 | Wing | |
| 2,223,541 A | 12/1940 | Baker | |
| 2,266,706 A | 12/1941 | Fox et al. | |
| 2,283,333 A | 5/1942 | Martin | |
| 2,292,381 A | 8/1942 | Klagges | |
| 2,360,297 A | 10/1944 | Wing | |
| 2,375,770 A | 5/1945 | Dahlberg | |
| 2,383,098 A | 8/1945 | Wheaton | |
| 2,404,063 A | 7/1946 | Healy | |
| 2,430,023 A | 11/1947 | Longmaid | |
| 2,474,996 A | 7/1949 | Wallis | |
| 2,512,004 A | 6/1950 | Wing | |
| 2,521,657 A | 9/1950 | Severy | |
| 2,681,041 A | 6/1954 | Zodtner et al. | |
| 2,705,007 A | 3/1955 | Gerber | |
| 2,735,427 A | 2/1956 | Sullivan | |
| 2,764,946 A | 10/1956 | Henderson | |
| 2,764,979 A | 10/1956 | Henderson | |
| 2,779,623 A | 1/1957 | Eisenkraft | |
| 2,935,970 A | 5/1960 | Morse et al. | |
| 3,103,310 A | 9/1963 | Lang | |
| 3,325,031 A | 6/1967 | Singier | |
| 3,411,854 A | 11/1968 | Rosler et al. | |
| 3,515,348 A | 6/1970 | Coffman, Jr. | |
| 3,550,864 A | 12/1970 | East | |
| 3,558,052 A | 1/1971 | Dunn | |
| 3,561,444 A | 2/1971 | Boucher | |
| 3,563,415 A | 2/1971 | Ogle | |
| 3,680,954 A | 8/1972 | Frank | |
| 3,719,328 A | 3/1973 | Hindman | |
| 3,738,574 A | 6/1973 | Guntersdorfer et al. | |
| 3,771,982 A | 11/1973 | Dobo | |
| 3,790,079 A * | 2/1974 | Berglund et al. | 239/3 |
| 3,804,329 A | 4/1974 | Martner | |
| 3,812,854 A | 5/1974 | Michaels et al. | |
| 3,826,413 A | 7/1974 | Warren | |
| 3,838,686 A | 10/1974 | Szekely | |
| 3,842,833 A | 10/1974 | Ogle | |
| 3,861,386 A | 1/1975 | Harris et al. | |
| 3,865,106 A | 2/1975 | Palush | |
| 3,903,884 A | 9/1975 | Huston et al. | |
| 3,906,950 A | 9/1975 | Cocozza | |
| 3,908,654 A | 9/1975 | Lhoest et al. | |
| 3,950,760 A | 4/1976 | Rauch et al. | |
| 3,951,313 A | 4/1976 | Coniglione | |
| 3,958,249 A | 5/1976 | DeMaine et al. | |
| 3,970,250 A | 7/1976 | Drews | |
| 3,983,740 A | 10/1976 | Danel | |
| 3,993,223 A | 11/1976 | Welker, III et al. | |
| 4,005,435 A | 1/1977 | Lundquist et al. | |
| 4,020,834 A | 5/1977 | Bird | |
| 4,030,492 A | 6/1977 | Simburner | |
| 4,052,986 A | 10/1977 | Scaife | |
| 4,059,384 A | 11/1977 | Holland et al. | |
| D246,574 S | 12/1977 | Meierhoefer | |
| 4,076,021 A | 2/1978 | Thompson | |
| 4,083,368 A | 4/1978 | Freezer | |
| 4,094,317 A | 6/1978 | Wasnich | |
| 4,101,041 A | 7/1978 | Mauro, Jr. et al. | |
| 4,106,503 A | 8/1978 | Rosenthal et al. | |
| 4,109,174 A | 8/1978 | Hodgson | |
| 4,113,809 A | 9/1978 | Abair et al. | |
| D249,958 S | 10/1978 | Meierhoefer | |
| 4,119,096 A | 10/1978 | Drews | |
| 4,121,583 A | 10/1978 | Chen | |
| 4,127,123 A | 11/1978 | Bird | |
| 4,159,803 A | 7/1979 | Cameto et al. | |
| 4,207,990 A | 6/1980 | Weiler et al. | |
| 4,210,155 A | 7/1980 | Grimes | |
| 4,226,236 A | 10/1980 | Genese | |
| 4,240,081 A | 12/1980 | Devitt | |
| 4,240,417 A | 12/1980 | Holever | |
| 4,248,227 A | 2/1981 | Thomas | |
| 4,261,512 A | 4/1981 | Zierenberg | |
| D259,213 S | 5/1981 | Pagels | |
| 4,268,460 A | 5/1981 | Boiarski et al. | |
| 4,294,407 A | 10/1981 | Reichl et al. | |
| 4,298,045 A | 11/1981 | Weiler et al. | |
| 4,299,784 A | 11/1981 | Hense | |
| 4,300,546 A | 11/1981 | Kruber | |
| 4,301,093 A | 11/1981 | Eck | |
| 4,319,155 A | 3/1982 | Makai et al. | |
| 4,323,064 A | 4/1982 | Hoenig et al. | |
| 4,328,798 A | 5/1982 | Isaacson | |
| 4,334,531 A | 6/1982 | Reichl et al. | |
| 4,336,544 A | 6/1982 | Donald et al. | |
| 4,338,576 A | 7/1982 | Takahashi et al. | |
| 4,340,044 A | 7/1982 | Levy et al. | |
| 4,368,476 A | 1/1983 | Uehara et al. | |
| 4,368,850 A | 1/1983 | Szekely | |
| 4,374,707 A | 2/1983 | Pollack | |
| 4,389,071 A | 6/1983 | Johnson, Jr. et al. | |
| 4,408,719 A | 10/1983 | Last | |
| 4,428,802 A | 1/1984 | Kanai et al. | |
| 4,431,136 A | 2/1984 | Janner et al. | |
| 4,454,877 A | 6/1984 | Miller et al. | |
| 4,465,234 A | 8/1984 | Maehara et al. | |
| 4,474,251 A | 10/1984 | Johnson, Jr. | |
| 4,474,326 A | 10/1984 | Takahashi | |
| 4,475,113 A | 10/1984 | Lee et al. | |
| 4,479,609 A | 10/1984 | Maeda et al. | |
| 4,484,577 A | 11/1984 | Sackner et al. | |
| 4,502,481 A | 3/1985 | Christian | |
| 4,512,341 A | 4/1985 | Lester | |
| 4,530,464 A | 7/1985 | Yamamoto et al. | |
| 4,533,082 A | 8/1985 | Maehara et al. | |
| 4,539,575 S | 9/1985 | Nilsson | |
| 4,544,933 A | 10/1985 | Heinzl | |
| 4,546,361 A | 10/1985 | Brescia et al. | |
| 4,550,325 A * | 10/1985 | Viola | 347/68 |
| 4,566,452 A | 1/1986 | Farr | |
| 4,591,883 A | 5/1986 | Isayama | |
| 4,593,291 A | 6/1986 | Howkins | |
| 4,605,167 A | 8/1986 | Maehara | |
| 4,613,326 A | 9/1986 | Szware | |
| 4,620,201 A | 10/1986 | Heinzl et al. | |
| 4,628,890 A | 12/1986 | Freeman | |
| 4,632,311 A | 12/1986 | Nakane et al. | |
| 4,658,269 A | 4/1987 | Rezanka | |
| 4,659,014 A | 4/1987 | Soth et al. | |
| 4,677,975 A | 7/1987 | Edgar et al. | |
| 4,678,680 A | 7/1987 | Abowitz | |
| 4,679,551 A | 7/1987 | Anthony | |
| 4,681,264 A | 7/1987 | Johnson, Jr. | |
| 4,693,853 A | 9/1987 | Falb et al. | |
| 4,702,418 A | 10/1987 | Carter et al. | |
| 4,722,906 A | 2/1988 | Guire | |
| 4,753,579 A | 6/1988 | Murphy | |
| 4,773,411 A | 9/1988 | Downs | |
| 4,790,479 A | 12/1988 | Matsumoto et al. | |

(56) References Cited

U.S. PATENT DOCUMENTS

| | | |
|---|---|---|
| 4,793,339 A | 12/1988 | Matsumoto et al. |
| 4,796,807 A | 1/1989 | Bendig et al. |
| 4,799,622 A | 1/1989 | Ishikawa et al. |
| 4,805,609 A | 2/1989 | Roberts et al. |
| 4,819,629 A | 4/1989 | Jonson |
| 4,819,834 A | 4/1989 | Thiel |
| 4,826,080 A | 5/1989 | Ganser |
| 4,826,759 A | 5/1989 | Guire et al. |
| 4,828,886 A | 5/1989 | Hieber |
| 4,843,445 A | 6/1989 | Stemme |
| 4,849,303 A | 7/1989 | Graham et al. |
| 4,850,534 A | 7/1989 | Takahashi et al. |
| 4,852,563 A | 8/1989 | Gross |
| 4,865,006 A | 9/1989 | Nogi et al. |
| 4,871,489 A | 10/1989 | Ketcham |
| 4,872,553 A | 10/1989 | Suzuki et al. |
| 4,877,989 A | 10/1989 | Drews et al. |
| 4,888,516 A * | 12/1989 | Daeges et al. ............ 310/323.01 |
| 4,922,901 A | 5/1990 | Brooks et al. |
| 4,926,915 A | 5/1990 | Deussen et al. |
| 4,934,358 A | 6/1990 | Nilsson et al. |
| 4,951,661 A | 8/1990 | Sladek |
| 4,954,225 A | 9/1990 | Bakewell |
| 4,957,239 A | 9/1990 | Tempelman |
| 4,964,521 A | 10/1990 | Wieland et al. |
| D312,209 S | 11/1990 | Morrow et al. |
| 4,968,299 A | 11/1990 | Ahlstrand et al. |
| 4,971,665 A | 11/1990 | Sexton |
| 4,973,493 A | 11/1990 | Guire |
| 4,976,259 A | 12/1990 | Higson et al. |
| 4,979,959 A | 12/1990 | Guire |
| 4,994,043 A | 2/1991 | Ysebaert |
| 5,002,048 A | 3/1991 | Makiej, Jr. |
| 5,002,582 A | 3/1991 | Guire et al. |
| 5,007,419 A | 4/1991 | Weinstein et al. |
| 5,016,024 A | 5/1991 | Lam et al. |
| 5,021,701 A | 6/1991 | Takahashi et al. |
| 5,022,587 A | 6/1991 | Hochstein |
| 5,024,733 A | 6/1991 | Abys et al. |
| 5,046,627 A | 9/1991 | Hansen |
| 5,062,419 A | 11/1991 | Rider |
| 5,063,396 A | 11/1991 | Shiokawa et al. |
| 5,063,922 A | 11/1991 | Hakkinen |
| 5,073,484 A | 12/1991 | Swanson et al. |
| 5,076,266 A | 12/1991 | Babaev |
| 5,080,093 A | 1/1992 | Raabe et al. |
| 5,080,649 A | 1/1992 | Vetter |
| 5,086,765 A | 2/1992 | Levine |
| 5,086,785 A | 2/1992 | Gentile et al. |
| 5,115,803 A | 5/1992 | Sioutas |
| 5,115,971 A | 5/1992 | Greenspan et al. |
| D327,008 S | 6/1992 | Friedman |
| 5,122,116 A | 6/1992 | Kriesel et al. |
| 5,129,579 A | 7/1992 | Conte |
| 5,134,993 A | 8/1992 | Van Der Linden et al. |
| 5,139,016 A | 8/1992 | Waser |
| 5,140,740 A | 8/1992 | Weigelt |
| 5,147,073 A | 9/1992 | Cater |
| 5,152,456 A * | 10/1992 | Ross et al. ................ 239/102.2 |
| 5,157,372 A | 10/1992 | Langford |
| 5,164,740 A | 11/1992 | Ivri |
| 5,169,029 A | 12/1992 | Behar et al. |
| 5,169,740 A | 12/1992 | Ushirogouchi et al. |
| 5,170,782 A | 12/1992 | Kocinski |
| 5,180,482 A | 1/1993 | Abys et al. |
| 5,186,164 A | 2/1993 | Raghuprasad |
| 5,186,166 A | 2/1993 | Riggs et al. |
| 5,198,157 A | 3/1993 | Bechet |
| 5,201,322 A | 4/1993 | Henry et al. |
| 5,213,860 A | 5/1993 | Laing |
| 5,217,148 A | 6/1993 | Cater |
| 5,217,492 A | 6/1993 | Guire et al. |
| 5,227,168 A | 7/1993 | Chvapil |
| 5,230,496 A | 7/1993 | Shillington et al. |
| 5,245,995 A | 9/1993 | Sullivan et al. |
| 5,248,087 A | 9/1993 | Dressler |
| 5,258,041 A | 11/1993 | Guire et al. |
| 5,261,601 A * | 11/1993 | Ross et al. ................ 239/102.2 |
| 5,263,992 A | 11/1993 | Guire |
| 5,279,568 A | 1/1994 | Cater |
| 5,297,734 A | 3/1994 | Toda |
| 5,299,739 A | 4/1994 | Takahashi et al. |
| 5,303,854 A | 4/1994 | Cater |
| 5,309,135 A | 5/1994 | Langford |
| 5,312,281 A | 5/1994 | Takahashi et al. |
| 5,313,955 A | 5/1994 | Rodder |
| 5,319,971 A | 6/1994 | Osswald et al. |
| 5,320,603 A | 6/1994 | Vetter et al. |
| 5,322,057 A | 6/1994 | Raabe et al. |
| 5,342,011 A | 8/1994 | Short |
| 5,342,504 A | 8/1994 | Hirano et al. |
| 5,347,998 A | 9/1994 | Hodson et al. |
| 5,348,189 A | 9/1994 | Cater |
| 5,350,116 A | 9/1994 | Cater |
| 5,355,872 A | 10/1994 | Riggs et al. |
| 5,357,946 A | 10/1994 | Kee et al. |
| 5,372,126 A | 12/1994 | Blau |
| 5,383,906 A | 1/1995 | Burchett et al. |
| 5,388,571 A | 2/1995 | Roberts et al. |
| 5,392,768 A | 2/1995 | Johansson et al. |
| 5,396,883 A | 3/1995 | Knupp et al. |
| 5,414,075 A | 5/1995 | Swan et al. |
| 5,415,161 A | 5/1995 | Ryder |
| 5,419,315 A | 5/1995 | Rubsamen |
| 5,426,458 A | 6/1995 | Wenzel et al. |
| 5,431,155 A | 7/1995 | Marelli |
| 5,435,282 A * | 7/1995 | Haber et al. ............ 128/200.16 |
| 5,435,297 A | 7/1995 | Klein |
| 5,437,267 A | 8/1995 | Weinstein et al. |
| 5,445,141 A | 8/1995 | Kee et al. |
| D362,390 S | 9/1995 | Weiler |
| 5,449,502 A | 9/1995 | Igusa et al. |
| 5,452,711 A | 9/1995 | Gault |
| 5,458,135 A | 10/1995 | Patton et al. |
| 5,458,289 A | 10/1995 | Cater |
| 5,474,059 A | 12/1995 | Cooper |
| 5,477,992 A | 12/1995 | Jinks et al. |
| 5,479,920 A | 1/1996 | Piper et al. |
| 5,485,850 A | 1/1996 | Dietz |
| 5,487,378 A | 1/1996 | Robertson et al. |
| 5,489,266 A | 2/1996 | Grimard |
| 5,497,944 A | 3/1996 | Weston et al. |
| D369,212 S | 4/1996 | Snell |
| 5,511,726 A | 4/1996 | Greenspan et al. |
| 5,512,329 A | 4/1996 | Guire et al. |
| 5,512,474 A | 4/1996 | Clapper et al. |
| 5,515,841 A | 5/1996 | Robertson et al. |
| 5,515,842 A | 5/1996 | Ramseyer et al. |
| 5,516,043 A | 5/1996 | Manna et al. |
| 5,518,179 A | 5/1996 | Humberstone et al. |
| 5,529,055 A | 6/1996 | Gueret |
| 5,533,497 A | 7/1996 | Ryder |
| 5,537,997 A | 7/1996 | Mechlenburg et al. |
| 5,542,410 A | 8/1996 | Goodman et al. |
| 5,549,102 A | 8/1996 | Lintl et al. |
| 5,560,837 A | 10/1996 | Trueba |
| 5,563,056 A | 10/1996 | Swan et al. |
| D375,352 S | 11/1996 | Bologna |
| 5,579,757 A | 12/1996 | McMahon et al. |
| 5,582,330 A | 12/1996 | Iba |
| 5,584,285 A | 12/1996 | Salter et al. |
| 5,586,550 A | 12/1996 | Ivri et al. |
| 5,588,166 A | 12/1996 | Burnett |
| 5,601,077 A | 2/1997 | Imbert |
| 5,605,659 A * | 2/1997 | Moynihan et al. ............ 264/430 |
| 5,609,798 A | 3/1997 | Liu et al. |
| 5,632,878 A | 5/1997 | Kitano |
| 5,635,096 A | 6/1997 | Singer et al. |
| 5,637,460 A | 6/1997 | Swan et al. |
| 5,647,349 A | 7/1997 | Ohki et al. |
| 5,653,227 A | 8/1997 | Barnes et al. |
| 5,654,007 A | 8/1997 | Johnson et al. |
| 5,654,162 A | 8/1997 | Guire et al. |
| 5,654,460 A | 8/1997 | Rong |

(56) References Cited

U.S. PATENT DOCUMENTS

| | | |
|---|---|---|
| 5,657,926 A | 8/1997 | Toda |
| 5,660,166 A | 8/1997 | Lloyd |
| 5,664,557 A | 9/1997 | Makiej et al. |
| 5,664,706 A | 9/1997 | Cater |
| 5,665,068 A | 9/1997 | Takamura |
| 5,666,946 A | 9/1997 | Langenback |
| 5,670,999 A | 9/1997 | Takeuchi et al. |
| 5,685,491 A | 11/1997 | Marks et al. |
| 5,692,644 A | 12/1997 | Gueret |
| 5,694,923 A | 12/1997 | Hete et al. |
| 5,707,818 A | 1/1998 | Chudzik et al. |
| 5,709,202 A | 1/1998 | Lloyd et al. |
| 5,714,360 A | 2/1998 | Swan et al. |
| 5,714,551 A | 2/1998 | Bezwada et al. |
| 5,718,222 A | 2/1998 | Lloyd et al. |
| D392,184 S | 3/1998 | Weiler |
| 5,724,957 A | 3/1998 | Rubsamen et al. |
| 5,744,515 A | 4/1998 | Clapper |
| 5,750,647 A | 5/1998 | Eyre et al. |
| 5,752,502 A | 5/1998 | King |
| 5,755,218 A | 5/1998 | Johansson et al. |
| 5,758,637 A | 6/1998 | Ivri et al. |
| 5,775,506 A | 7/1998 | Grabenkort |
| 5,788,665 A | 8/1998 | Sekins |
| 5,788,819 A | 8/1998 | Onishi et al. |
| 5,790,151 A | 8/1998 | Mills |
| 5,810,004 A | 9/1998 | Ohki et al. |
| 5,819,726 A | 10/1998 | Rubsamen et al. |
| 5,819,730 A | 10/1998 | Stone et al. |
| 5,823,179 A | 10/1998 | Grychowski et al. |
| 5,823,428 A | 10/1998 | Humberstone et al. |
| 5,829,723 A | 11/1998 | Brunner et al. |
| 5,836,515 A | 11/1998 | Fonzes |
| 5,838,350 A | 11/1998 | Newcombe et al. |
| 5,839,617 A | 11/1998 | Cater et al. |
| 5,842,468 A | 12/1998 | Denyer et al. |
| 5,862,802 A | 1/1999 | Bird |
| 5,865,171 A | 2/1999 | Cinquin |
| 5,878,900 A | 3/1999 | Hansen |
| 5,893,515 A | 4/1999 | Hahn et al. |
| 5,894,841 A | 4/1999 | Voges |
| 5,897,008 A | 4/1999 | Hansen |
| 5,910,698 A | 6/1999 | Yagi |
| 5,915,377 A | 6/1999 | Coffee |
| 5,918,637 A | 7/1999 | Fleischman |
| 5,925,019 A | 7/1999 | Ljungquist |
| 5,938,117 A | 8/1999 | Ivri |
| 5,950,619 A | 9/1999 | Van Der Linden et al. |
| 5,954,268 A | 9/1999 | Joshi et al. |
| 5,960,792 A | 10/1999 | Lloyd et al. |
| 5,964,417 A | 10/1999 | Amann et al. |
| 5,970,974 A | 10/1999 | Van Der Linden et al. |
| 5,976,344 A | 11/1999 | Abys et al. |
| 5,993,805 A | 11/1999 | Sutton et al. |
| 6,000,396 A | 12/1999 | Melker et al. |
| 6,007,518 A | 12/1999 | Kriesel et al. |
| 6,012,450 A | 1/2000 | Rubsamen |
| 6,014,970 A | 1/2000 | Ivri et al. |
| 6,026,809 A | 2/2000 | Abrams et al. |
| 6,029,666 A | 2/2000 | Aloy et al. |
| 6,032,665 A | 3/2000 | Psaros |
| 6,037,587 A | 3/2000 | Dowell et al. |
| 6,039,696 A | 3/2000 | Bell |
| 6,045,215 A | 4/2000 | Coulman |
| 6,045,874 A | 4/2000 | Himes |
| 6,047,818 A | 4/2000 | Warby et al. |
| 6,055,869 A | 5/2000 | Stemme et al. |
| 6,060,128 A | 5/2000 | Kim et al. |
| 6,062,212 A | 5/2000 | Davison et al. |
| 6,068,148 A | 5/2000 | Weiler |
| 6,085,740 A | 7/2000 | Ivri et al. |
| 6,096,011 A | 8/2000 | Trombley, III et al. |
| 6,105,877 A | 8/2000 | Coffee |
| 6,106,504 A | 8/2000 | Urrutia |
| 6,116,234 A | 9/2000 | Genova et al. |
| 6,123,413 A | 9/2000 | Agarwal et al. |
| 6,139,674 A | 10/2000 | Markham et al. |
| 6,142,146 A | 11/2000 | Abrams et al. |
| 6,145,963 A | 11/2000 | Pidwerbecki et al. |
| 6,146,915 A | 11/2000 | Pidwerbecki et al. |
| 6,152,130 A | 11/2000 | Abrams et al. |
| 6,155,676 A | 12/2000 | Etheridge et al. |
| 6,158,431 A | 12/2000 | Poole |
| 6,161,536 A | 12/2000 | Redmon et al. |
| 6,163,588 A | 12/2000 | Matsumoto et al. |
| 6,182,662 B1 | 2/2001 | McGhee |
| 6,186,141 B1 | 2/2001 | Pike et al. |
| 6,196,218 B1 | 3/2001 | Voges |
| 6,196,219 B1 | 3/2001 | Hess et al. |
| 6,205,999 B1 | 3/2001 | Ivri et al. |
| 6,216,916 B1 | 4/2001 | Maddox et al. |
| 6,223,746 B1 | 5/2001 | Jewett et al. |
| 6,235,177 B1 | 5/2001 | Borland et al. |
| 6,254,219 B1 | 7/2001 | Agarwal et al. |
| 6,269,810 B1 | 8/2001 | Brooker et al. |
| 6,270,473 B1 | 8/2001 | Schwebel |
| 6,273,342 B1 | 8/2001 | Terada et al. |
| 6,293,474 B1 | 9/2001 | Helf et al. |
| 6,318,640 B1 | 11/2001 | Coffee |
| 6,328,030 B1 | 12/2001 | Kidwell et al. |
| 6,328,033 B1 | 12/2001 | Avrahami |
| 6,341,732 B1 | 1/2002 | Martin et al. |
| 6,358,058 B1 | 3/2002 | Strupat et al. |
| 6,367,470 B1 | 4/2002 | Denyer et al. |
| 6,382,522 B2 | 5/2002 | Tomkins et al. |
| 6,394,363 B1 | 5/2002 | Arnott et al. |
| 6,402,046 B1 | 6/2002 | Loser |
| 6,405,934 B1 | 6/2002 | Hess et al. |
| 6,427,682 B1 | 8/2002 | Klimowicz et al. |
| 6,443,146 B1 | 9/2002 | Voges |
| 6,443,366 B1 | 9/2002 | Hirota et al. |
| 6,450,419 B1 | 9/2002 | Martens et al. |
| 6,467,476 B1 | 10/2002 | Ivri et al. |
| 6,467,477 B1 | 10/2002 | Frank et al. |
| 6,530,370 B1 | 3/2003 | Heinonen |
| 6,540,153 B1 | 4/2003 | Ivri |
| 6,540,154 B1 | 4/2003 | Ivri et al. |
| 6,543,443 B1 | 4/2003 | Klimowicz et al. |
| 6,546,927 B2 | 4/2003 | Litherland et al. |
| 6,550,472 B2 | 4/2003 | Litherland et al. |
| 6,554,201 B2 | 4/2003 | Klimowicz et al. |
| 6,581,595 B1 | 6/2003 | Murdock et al. |
| 6,615,824 B2 * | 9/2003 | Power ................... 128/200.14 |
| 6,629,646 B1 | 10/2003 | Ivri |
| 6,640,804 B2 | 11/2003 | Ivri |
| 6,651,650 B1 | 11/2003 | Yamamoto et al. |
| 6,688,304 B2 | 2/2004 | Gonda et al. |
| 6,705,315 B2 | 3/2004 | Sullivan et al. |
| 6,705,316 B2 | 3/2004 | Blythe et al. |
| 6,725,858 B2 | 4/2004 | Loescher |
| 6,732,944 B2 | 5/2004 | Litherland et al. |
| 6,745,768 B2 | 6/2004 | Colla et al. |
| 6,745,770 B2 | 6/2004 | McAuliffe et al. |
| 6,755,189 B2 | 6/2004 | Ivri et al. |
| 6,769,626 B1 | 8/2004 | Haveri |
| 6,782,886 B2 | 8/2004 | Narayan et al. |
| 6,814,071 B2 | 11/2004 | Klimowicz et al. |
| 6,817,361 B2 | 11/2004 | Berthon-Jones |
| 6,840,240 B1 | 1/2005 | Berthon-Jones et al. |
| 6,845,770 B2 | 1/2005 | Klimowicz et al. |
| 6,851,626 B2 | 2/2005 | Patel et al. |
| 6,860,268 B2 | 3/2005 | Bohn et al. |
| 6,904,906 B2 | 6/2005 | Salter et al. |
| 6,915,962 B2 | 7/2005 | Power et al. |
| 6,921,020 B2 | 7/2005 | Ivri |
| 6,926,208 B2 | 8/2005 | Ivri |
| 6,948,491 B2 | 9/2005 | Loeffler et al. |
| 6,968,840 B2 | 11/2005 | Smith et al. |
| 7,032,590 B2 | 4/2006 | Loeffler et al. |
| 7,040,549 B2 | 5/2006 | Ivri et al. |
| 7,066,398 B2 | 6/2006 | Borland et al. |
| 7,083,112 B2 | 8/2006 | Ivri |
| 7,100,600 B2 | 9/2006 | Loeffler et al. |
| 7,108,197 B2 | 9/2006 | Ivri |

(56) References Cited

U.S. PATENT DOCUMENTS

| | | | |
|---|---|---|---|
| 7,174,888 B2 | 2/2007 | Ivri et al. |
| 7,195,011 B2 | 3/2007 | Loeffler et al. |
| 7,201,167 B2 | 4/2007 | Fink et al. |
| 7,267,121 B2 | 9/2007 | Ivri |
| 7,290,541 B2 | 11/2007 | Ivri et al. |
| 7,322,349 B2 | 1/2008 | Power |
| 2001/0013554 A1 | 8/2001 | Borland et al. |
| 2001/0015737 A1 | 8/2001 | Truninger et al. |
| 2001/0050317 A1* | 12/2001 | Denen ................. 239/102.1 |
| 2002/0011247 A1 | 1/2002 | Ivri et al. |
| 2002/0023650 A1 | 2/2002 | Gunaratnam et al. |
| 2002/0033178 A1 | 3/2002 | Farrell et al. |
| 2002/0036601 A1 | 3/2002 | Puckeridge et al. |
| 2002/0078958 A1 | 6/2002 | Stenzler |
| 2002/0104530 A1 | 8/2002 | Ivri et al. |
| 2002/0121274 A1 | 9/2002 | Borland et al. |
| 2002/0134372 A1 | 9/2002 | Loeffler et al. |
| 2002/0134374 A1 | 9/2002 | Loeffler et al. |
| 2002/0134375 A1 | 9/2002 | Loeffler et al. |
| 2002/0134377 A1 | 9/2002 | Loeffler et al. |
| 2002/0162551 A1 | 11/2002 | Litherland |
| 2002/0195107 A1 | 12/2002 | Smaldone |
| 2003/0140921 A1 | 7/2003 | Smith et al. |
| 2003/0145859 A1 | 8/2003 | Bohn et al. |
| 2003/0150445 A1 | 8/2003 | Power et al. |
| 2003/0150446 A1 | 8/2003 | Patel et al. |
| 2003/0226906 A1 | 12/2003 | Ivri |
| 2004/0000598 A1 | 1/2004 | Ivri |
| 2004/0004133 A1 | 1/2004 | Ivri et al. |
| 2004/0011358 A1 | 1/2004 | Smaldone et al. |
| 2004/0035413 A1 | 2/2004 | Smaldone et al. |
| 2004/0035490 A1 | 2/2004 | Power |
| 2004/0050947 A1 | 3/2004 | Power et al. |
| 2004/0139963 A1 | 7/2004 | Ivri et al. |
| 2004/0139968 A1 | 7/2004 | Loeffler et al. |
| 2004/0188534 A1 | 9/2004 | Litherland et al. |
| 2004/0194783 A1 | 10/2004 | McAuliffe et al. |
| 2004/0226561 A1 | 11/2004 | Colla et al. |
| 2004/0226566 A1 | 11/2004 | Gunaratnam et al. |
| 2004/0256488 A1 | 12/2004 | Loeffler et al. |
| 2005/0011514 A1 | 1/2005 | Power et al. |
| 2005/0039746 A1 | 2/2005 | Grychowski et al. |
| 2005/0139211 A1 | 6/2005 | Alston et al. |
| 2005/0150496 A1 | 7/2005 | Smaldone |
| 2005/0178471 A1 | 8/2005 | Power et al. |
| 2005/0199236 A1 | 9/2005 | Fink et al. |
| 2005/0211245 A1 | 9/2005 | Smaldone et al. |
| 2005/0211253 A1 | 9/2005 | Smaldone et al. |
| 2005/0217666 A1 | 10/2005 | Fink et al. |
| 2005/0220763 A1 | 10/2005 | Condos et al. |
| 2005/0229927 A1 | 10/2005 | Fink et al. |
| 2005/0235987 A1 | 10/2005 | Smaldone et al. |
| 2005/0284469 A1 | 12/2005 | Tobia et al. |
| 2006/0255174 A1 | 11/2006 | Ivri et al. |
| 2007/0023547 A1 | 2/2007 | Borland et al. |
| 2007/0075161 A1 | 4/2007 | Ivri |
| 2007/0083677 A1 | 4/2007 | Cecka et al. |
| 2007/0116649 A1 | 5/2007 | Charan et al. |
| 2007/0209659 A1 | 9/2007 | Ivri et al. |
| 2007/0267010 A1 | 11/2007 | Fink et al. |
| 2008/0017198 A1 | 1/2008 | Ivri |
| 2008/0060641 A1 | 3/2008 | Smith et al. |
| 2008/0142002 A1 | 6/2008 | Fink et al. |
| 2008/0149096 A1 | 6/2008 | Power |

FOREIGN PATENT DOCUMENTS

| | | |
|---|---|---|
| EP | 0 049 636 | 4/1982 |
| EP | 0 103 161 | 3/1984 |
| EP | 0 134 847 | 3/1985 |
| EP | 0 178 925 | 4/1986 |
| EP | 0 387 222 | 9/1990 |
| EP | 0 432 992 | 6/1991 |
| EP | 0 476 991 | 3/1992 |
| EP | 0 480 615 | 4/1992 |
| EP | 0 510 648 | 10/1992 |
| EP | 0 516 565 | 12/1992 |
| EP | 0 542 723 | 5/1993 |
| EP | 0 933 138 | 4/1999 |
| EP | 0 923 957 | 6/1999 |
| EP | 1 142 600 | 10/2001 |
| GB | 973 458 | 10/1964 |
| GB | 1 454 597 | 11/1976 |
| GB | 2 073 616 | 10/1981 |
| GB | 2 101 500 | 1/1983 |
| GB | 2 177 623 | 1/1987 |
| GB | 2 240 494 | 7/1991 |
| GB | 2 272 389 | 5/1994 |
| JP | 57-023852 | 2/1982 |
| JP | 57-105608 | 7/1982 |
| JP | 58-061857 | 4/1983 |
| JP | 58-139757 | 8/1983 |
| JP | 59-142163 | 8/1984 |
| JP | 60-004714 | 1/1985 |
| JP | 61-008357 | 1/1986 |
| JP | 61-215059 | 9/1986 |
| JP | 02-135169 | 5/1990 |
| JP | 02-189161 | 7/1990 |
| JP | 60-07721 | 1/1994 |
| WO | WO 92/07600 | 5/1992 |
| WO | WO 92/11050 | 9/1992 |
| WO | WO 92/17231 | 10/1992 |
| WO | WO 93/01404 | 1/1993 |
| WO | WO 93/10910 | 6/1993 |
| WO | WO 94/09912 | 5/1994 |
| WO | WO 96/09229 | 3/1996 |
| WO | WO 99/17888 | 4/1999 |
| WO | WO 00/37132 | 6/2000 |
| WO | WO 0051747 | 9/2000 |

OTHER PUBLICATIONS

PCT Written Opinion, mail date Nov. 19, 2007, Intl Filing date Apr. 17, 2006.

Abys, et al., "Annealing Behavior of Palladium-Nickel Alloy Electrodeposits," Plating and Surface Finishing, Aug. 1996; p. 1-7.

Allen, "Particle Size Measurement," Chapman and Hall, 3 ed., 1981; p. 167-169.

Ashgriz, et al., "Development of a Controlled Spray Generator," Rev. Sci. Instrum., 1987; vol. 58 ( No. 7), p. 1291-1296.

Berggren, "Pilot Study of Nebulized Surfactant Therapy for Neonatal Respiratory Distress Syndrome," Acta Paediatr, Taylor & Francis, ISSN 0803-5253 (Sweden), 2000; 89: p. 460-464.

Berglund, et al., "Generation of Monodisperse Aerosol Standards," Environ. Sci. Technology, Feb. 1973; vol. 7 ( No. 2), p. 147-153.

Cipolla, et al., "Assessment of Aerosol Delivery Systems for Recombinant Human Deoxyribonuclease," S.T.P. Pharma Sciences, 1994; vol. 4 ( No. 1), p. 50-62.

Cipolla, et al., "Characterization of Aerosols of Human Recombinant Deoxyribonuclease I (rhDNase) Generated by Neulizers," Pharmaceutical Research II, 1994; p. 491-498.

Dogan, Thesis: "Flexional 'Moonie and Cymbal' Actuators," Penn State University, 1994.

Duarte, et al., "Inhalation Therapy During Mechanical Ventilation," Respiratory Care Clinics of North America, Aerosol Therapy, Jun. 2001; vol. 7 ( No. 2), p. 233-259.

Fink, et al., "Aerosol Drug Therapy," Clinical Practice in Respiratory Care, Chapter 12, 1999; p. 308-342.

Fink, et al., "Aerosol Therapy in Mechanically Ventilated Patients: Recent Advances and New Techniques," Seminars in Respiratory and Critical Care Medicine, 2000; vol. 21 ( No. 3), p. 183-201.

Fink, et al., "Diagram from and abstract of article entitled Optimizing efficiency of nebulizers during mechanical ventilation: The effect of placement and type of ventilator circuit," Chest, Oct. 1999; p. 116:312S.

Gaiser Tool, Company catalog, 1990; p. 26, 29-30.

Gonda, "Therapeutic Aerosols," Pharmaceutics, The Science of Dosage Form Design, Editor: M.E. Aulton, 1988; p. 341-358.

Hancock, et al., "Molecular Mobility of Amorphous Pharmaceutical Solids Below Their Glass Transition Temperatures," Pharmaceutical Research 12, 1995; p. 799-806.

(56) References Cited

OTHER PUBLICATIONS

Heyder, et al., "Deposition of particles in the human respiratory tract in the size range 0.005-15 microns," J. Aerosol Sci., 1986; vol. 17, p. 811-825.

Hickey, "Pharmaceutical Inhalation Aerosol Tehcnology," Drugs and the Pharmaceutical Science, 1992; vol. 54, p. 172-173.

Hikayama, et al., "Ultrasonic Atomizer with Pump Function," Tech. Rpt. IEICE Japan, 1988; US88-74:25. (No English Translation Available).

Jorch, Letter to the Editor, "Surfactant Aerosol Treatment of Respiratory Distress Syndrome in Spontaneously Breathing Premature Infants," Pediatric Pulmonology, Wiley-Liss, Inc., 1997; vol. 24, p. 222-224.

Maehara, et al., "Atomizing rate control of a multi-pinhole-plate ultrasonic atomizer," J. Acoustical Soc., Japan, 1988; vol. 44 (No. 2), p. 116-121.

Maehara, et al., "Influence of the vibrating system of a multipinhole-plate ultrasonic nebulizer on its performance," Review of Scientific Instruments, Nov. 1986; vol. 57 (No. 1), p. 2870-2876.

Maehara, et al., "Influence of liquid's physical properties on the characteristics of a multi-pinhole-plate ultrasonic atomizer," J. Acoustical Soc. Japan, 1988; vol. 44, No. 6, p. 425-431.

Maehara, et al., "Optimum Design Procedure for Multi-Pinhole-Plate Ultrasonic Atomizer," Japanese J. of Applied Physics, 1987; vol. 26, Supp. 26-1, p. 215-217.

Nogi, et al., "Mixture Formation of Fuel Injection System in Gasoline Engine," Nippon Kikai Gakkai Zenkoku Taikai Koenkai Koen Ronbunshu, 1991; vol. 69, p. 660-662.

Palla Tech Pd and Pd Alloy Processes—Procedure for the Analysis of Additive IVS in Palla Tech Plating Solutions by HPLC, Technical Bulletin, Electroplating Chemicals & Services, 029-A, Lucent Tecnologies, 1996; p. 1-5.

Siemens, Servo Ultra Nebulizer 345 Operating Manual, p. 1-23.

Smaldone, "Aerosolized Antibiotics: Current and Future," Respiratory Care, vol. 45, No. 6, p. 667-675.

Smedsass-Lofvenbert, "Nebulization of Drugs in a Nasal CPAP System," Scandinavian University Press, 1999; Acta Paediatr 88: 89-82, Sweden.

Ueha, et al., "Mechanism of Ultrasonic Atomization Using a Multi-Pinhole Plate," J. Acoust. Soc. Japan, 1985; p. 21-26, (E)6,1.

Wehl, "Ink-Jet Printing: The Present State of the Art," for Siemens AG, 1989.

* cited by examiner

VIBRATION SYSTEMS AND METHODS

CROSS-REFERENCE TO RELATED APPLICATIONS

This application is a 35 USC §371 application of International Application No. PCT/US2006/014654 filed Apr. 17, 2006, designating the United States, which claims priority to U.S. Application No. 60/684,720 filed May 25, 2005, now abandoned, both of which are hereby incorporated by reference in their entirety.

BACKGROUND OF THE INVENTION

This invention relates generally to a vibration system that efficiently transfers radial vibration from a vibration-inducing member to produce axial vibration in a vibratable member through a support member that filters out undesirable vibration. In preferred embodiments, a piezoelectric transducer imparts ultrasonic oscillation to a vibratable plate, particularly a vibrating aperture (orifice) plate of an aerosol generator device, wherein the vibrating plate is perforated with holes and is operable in a fluid medium. The invention may also useful in the field of ultrasonic wave transmission in a fluid medium including, but not limited to, underwater sonar, depth sonar and obstacle detecting sonar.

Devices wherein a circular aperture plate is vibrated using a piezoelectric transducer in the form of a ring are well-known in the art. For example, in Maehara U.S. Pat. No. 4,605,167, a vibratable plate having at least one nozzle opening therein is secured to a rigid housing and a piezoelectric ring is secured to the vibratable plate for inducing therein a displacement to discharge a small quantity of liquid through the nozzle opening. In other devices described in the art, a circular vibratable plate is directly bonded to the piezoelectric ring and covers the central opening in the piezoelectric ring; for example, as described in Toda U.S. Pat. No. 5,297,734. As other examples, Humberstone et al U.S. Pat. No. 5,518,179, Ross et al U.S. Pat. No. 5,261,601 and Davison et al U.S. Pat. No. 6,062,212 describe vibrating devices wherein a circular vibratable plate is mounted over the central opening of a thin annular member, or "washer", which is bonded to a piezoelectric ring. When actuated, the piezoelectric ring vibrates radially to cause the washer to operate in a "bending mode" that vibrates the vibratable plate in the axial direction. When these types of devices are manufactured the components must be carefully aligned concentrically with each other when the vibratable plate is attached to the washer and the washer is positioned over the opening in the piezoelectric ring.

Installing an ultrasonic transducer directly onto a rigid frame or housing, such as taught by Maehara, is also problematic. The reason is that the entire body of the transducer vibrates, with some portions vibrating at a small amplitude and some portions vibrating at an amplified amplitude. When the transducer is installed on the rigid fixture, the oscillation amplitude is reduced. Another problem with prior art arrangements is that the piezoelectric ring naturally vibrates in 3 directions (i.e., X, Y and Z axes) and transmits such vibration to the vibrating plate. The vibrations that are transmitted to the plate are superimposed and the contribution of the axial vibration may be canceled or partially canceled out. It is therefore desirable to filter out the undesirable vibration of the piezoelectric element and to use only vibration in a single direction, e.g. the axial direction. Attempts to address this problem have included mounting the vibratable plate on resilient retainer members, or "fingers", e.g. as described in Martens III et al U.S. Pat. No. 6,450,419; supporting a bimorph-type transducer on rubber O-rings, e.g. as described in Ross et al U.S. Pat. No. 5,261,601 and Humberstone et al U.S. Pat. No. 5,518,179; and holding the piezoelectric ring in place with a grommet, e.g. as described in Helf et al U.S. Pat. No. 6,293,474 and Tomkins et al U.S. Pat. No. 6,382,522.

The above-described devices translate the radial vibration of a piezoelectric ring to axial vibration of a perforate plate to disperse a liquid as an aerosol. In another type of device, the piezoelectric transducer may be tubular and may expand and contract axially (in the direction of the central axis of the tube) to move a perforate plate. For example, see Newcombe et al U.S. Pat. No. 5,838,350.

Generally, in a piezoelectric transducer that operates in a fluid medium, such as those used in aerosolizers, there is a need to separate the piezoelectric element from the vibratable element so that the vibratable element can be submerged in liquid and the piezoelectric element can be electrically insulated from the liquid. In some cases, such insulation may be provided by encasing the piezoelectric element with elastomer material. Such material, while providing electrical insulation, also has energy-absorbing characteristics that dampen the oscillation amplitude of the piezoelectric transducer and therefore has an adverse effect of the efficiency of the device.

There are currently a wide variety of aerosolizers and nebulizers. Of particular interest are those which vibrate an aperture plate or other element to produce the aerosol. Examples of some of these aerosolizers are described in U.S. Pat. Nos. 5,169,740, 5,938,117, 6,540,154, 5,586,550, 5,750,647, 6,467,476, 6,014,970, 6,755,189, 6,814,071, 6,554,201, 6,732,944, 6,615,824, 6,845,770, and 6,851,626, each of which is incorporated herein by reference in its entirety. One issue with aerosolizers (especially those used for medical applications using highly corrosive liquids) is contamination and corrosion of parts. Certain parts of the aerosolizer that are exposed to liquids may need to be washed or disposed of in order to keep the aerosolizer in good working order. Many of these parts are difficult to clean and, since piezoelectric transducers and their associated electronics can be relatively expensive, making them disposable may not be economically feasible. Therefore, it may be desirable to make certain aerosolizer components removable or replaceable.

BRIEF SUMMARY OF THE INVENTION

One or more embodiments of the present invention are directed to a vibration system that efficiently transfers radial vibration from a vibration-inducing member to produce axial vibration in a vibratable member through a support member that filters out undesirable vibration. In one particular arrangement, the vibration-inducing member may be an annular piezoelectric transducer having a central opening, the vibratable member may be a thin circular plate and the support member may have a circular cross-section for holding the circular plate; however, the components may also possibly have other shapes. In other arrangements, the vibration-inducing member is separable from the other structures so that it may be reused for other applications. In addition, other arrangements of the present invention effectively isolate the vibration-inducing member from contact with liquids and is therefore particularly adapted for operation in a fluid medium, e.g. in an aerosolizer environment. Still further, the present invention provides a method for self-aligning the components of a vibration system comprising a piezoelectric ring and a circular vibratable plate so as make manufacture of the system simple and inexpensive.

In one or more embodiments, the vibration system of the present invention comprises a thin circular vibratable plate, a tubular member holding the vibratable plate and a piezoelectric ring coupled to the tubular member. The vibratable plate may be concentrically disposed within the lumen of a thin-walled tubular member; and a piezoelectric ring may be concentrically positioned about the outer circumference of the tubular member at the location of the vibratable plate. The piezoelectric ring is expandable and contractable in the radial direction, which in turn causes the walls of the tubular member to expand and contract in the radial direction. This movement of the tubular member walls expands and contracts the outer circumference of the plate causing its middle region to oscillate (i.e. vibrate) in the axial direction. Since the outer circumference of the vibratable plate of the present invention is positioned within the central opening of the piezoelectric ring in alignment with its central plane, in contrast to prior systems wherein a surface of the vibratable plate (or concentric washer around the plate) is secured at the surface of the piezoelectric ring across the central opening of the piezoelectric ring, the radial load produced by the piezoelectric ring is more symmetrically applied to the vibratable plate of the present invention.

In one embodiment, the vibratable plate may be an aperture plate that includes a plurality of tapered apertures and is preferably dome-shaped. The aperture plate may be coupled to a mounting structure disposed within the lumen of the tubular member that holds the aperture plate perpendicular to the central axis of the tubular member.

In another embodiment, the tubular member may be fabricated from a corrosive-resistant metallic material, e.g. a palladium/nickel alloy or stainless steel, and have flexible thin walls, e.g. less than 0.5 mm in thickness. In other embodiments, the tubular member may comprise a plastic material, and may include at least one resilient segment, e.g. an elastomer, disposed therein that allows the tubular member to be compressed and expanded by the piezoelectric ring. In another embodiment, the piezoelectric ring may be removable from the tubular member and re-used for other applications. For example, the tubular member may be tapered to form a "taper lock" wherein the piezoelectric ring is press-fitted with the tubular member. In a still further embodiment, the piezoelectric ring may be permanently bonded to the tubular member to form an integral unit.

In one embodiment, a tubular member containing an aperture plate may be operably coupled to a reservoir of liquid, or the reservoir may be an integral part of the tubular member, so that liquid is supplied to the aperture plate within the tubular member. In this way, when the aperture plate is vibrated in accordance with the invention, liquid droplets are ejected from the aperture plate in the form of an aerosol. Optionally, a ring may be disposed about the outer periphery of the piezoelectric ring to assist in vibrating the aperture plate at its resonant frequency. In embodiments wherein the tubular member and the piezoelectric ring are not integrated with the reservoir, O-rings or other seals may be provided between the reservoir and the tubular member to serve as liquid-tight seals that prevent contamination of the piezoelectric ring, and also provide damping the piezoelectric ring and the aerosolizer housing, thereby increasing the efficiency of the system. In another embodiment, the tubular member may be "press-fitted" (i.e. form an "interference fit") with a discharge opening of the reservoir.

In one embodiment of the invention, the reservoir and the tubular member containing the aperture plate may be integrated as a single unit, and the piezoelectric ring may be slid over the reservoir of the aerosolizer to form a press-fit with the tubular member. In this way, the piezoelectric ring may be removed without potential contamination from substances within the reservoir or tubular member, or from aerosol produced by the aperture plate. In another embodiment, the piezoelectric ring and the tubular member may be bonded together as an integral unit.

The vibration system of the present invention may be incorporated into a variety of products and may be connected to power supplies, electronics to vibrate the vibration-inducing member, and the like. In one embodiment, the vibration system of the present invention is connected to a power supply using a first wire that makes electrical contact with a first surface of the piezoelectric ring and a second wire that makes electrical contact with a second surface of the vibration-inducing member. These wires may be located in grooves surrounding the outer surface of the housing in which the vibration system is located so that they are isolated from liquids in the reservoir and within the tubular member of the vibration system.

Examples of products that may employ the vibration system of the present invention include ventilators, continuous positive airway pressure (CPAP) systems, hand-held nebulizers and the like, as well as devices that utilize ultrasonic wave transmission in a fluid medium, such as, for example, various sonar devices. As one example, a ventilator circuit may comprise a length of tubing, and the vibration system of the present invention may be operably coupled to the tubing to introduce aerosol generated by the vibration system into the ventilator circuit. As another example, an aerosolizer may be constructed of a housing having a mouthpiece and the vibration system of the invention may be disposed in the housing so that liquid droplets produced by the vibrating aperture plate are ejected through the mouthpiece and into the respiratory system of the user.

One embodiment of the invention provides an exemplary method for making a vibration system comprising the steps of inserting a vibratable plate into a support structure that surrounds the plate; surrounding the support structure including vibratable plate with a vibration-inducing member that is configured to expand and contract radially; and actuating the vibration-inducing member to produce radial expansion and contraction against the support member to cause axial vibration of the vibratable plate.

In one particular embodiment, a method of making a vibration system comprises the steps of providing a tubular member with a lengthwise lumen, securing a circular vibratable plate within the lumen so that the vibratable plate is perpendicular to the central axis of the tubular member; providing a piezoelectric ring having a center opening; positioning the tubular member within the center opening of the piezoelectric ring so that outer circumference of the tubular member is in contact with the inner circumference of the opening and the vibration-inducing member surrounds the vibratable plate within the tubular member; and securing the vibration-inducing member to the tubular member.

In another embodiment, a method of vibrating a plate comprises the steps of inserting a vibratable plate in a support structure that surrounds the entire periphery of the plate, inserting the support structure including vibratable plate into the central opening of a vibration-inducing member that is configured to expand and contract radially, and actuating the vibration-inducing member to produce radial expansion and contraction against the support member that causes axial vibration of the vibratable plate.

In another embodiment, a method of treating a patient is provided, which comprises the steps of providing a vibration system comprising a circular vibratable aperture plate having an outer circumference, a tubular member concentrically disposed about the outer circumference of the vibratable plate, wherein the tubular member has an outer circumference, and an annular vibration-inducing member concentrically disposed about the outer circumference of the tubular member, wherein the vibration-inducing member is radially expandable and contractable to cause the aperture plate to vibrate in the axial direction; supplying a liquid medicament to the aperture plate via the tubular member; actuating the vibration-inducing member to vibrate the aperture plate and aerosolize the liquid medicament; and supplying the aerosol to a patient's respiratory system.

BRIEF DESCRIPTION OF THE DRAWINGS

FIG. 4b is a partial cross-sectional view of the aerosolizer shown in FIG. 4a.

FIG. 4c is a perspective view of the aerosolizer shown in FIG. 4a.

FIG. 7b is a cross-sectional side view of the aerosolizer of FIG. 7a.

DETAILED DESCRIPTION OF THE INVENTION

Figures 1A, 1B:
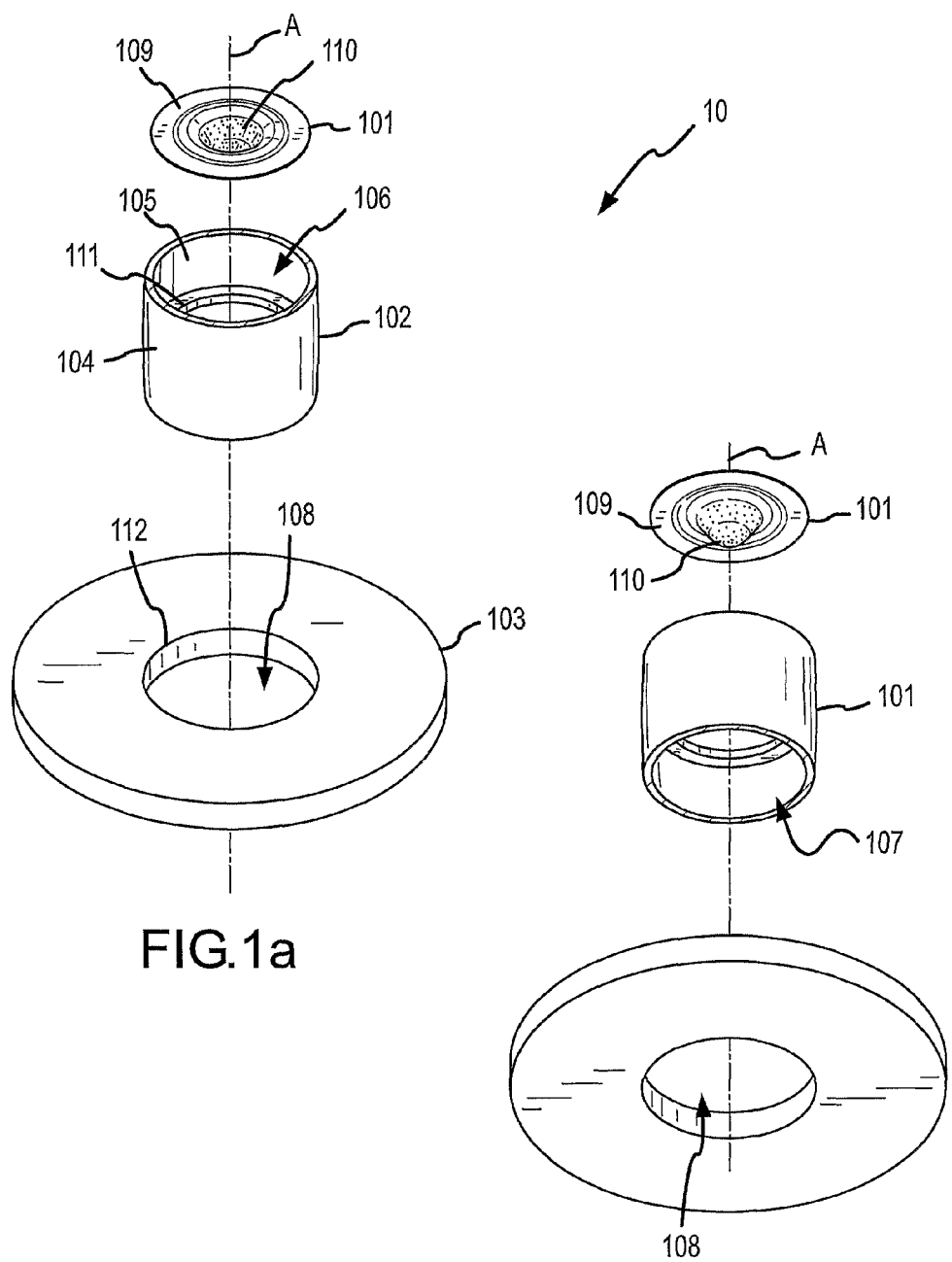
FIGS. 1a and 1b are exploded perspective views of a vibration system of the invention.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include the plural unless the content clearly dictates otherwise.

Reference herein to "one embodiment", "one version" or "one aspect" shall include one or more such embodiments, versions or aspects, unless otherwise clear from the context.

In one or more embodiments, the vibration system of the present invention comprises a vibratable plate, a support member surrounding the vibratable plate, and a vibration-inducing member surrounding the support member, wherein the vibration-inducing member is configured to radially expand and contract against the support member so as to produce axial vibration of the vibratable plate. The following detailed description is directed to one preferred embodiment of the invention wherein the vibratable plate is circular, the support member has a circular cross-section, e.g. a tubular member (cylindrical or tapered), into which the circular vibratable plate is disposed, and the vibration-inducing member is an annular disc having a central opening, i.e. a piezoelectric ring, into which the support member is disposed. However, it should be understood that the invention is not limited to this embodiment.

The tubular member may be manufactured from a corrosion-resistant metal, for example, stainless steel (preferably grades 316, 303 or 416), titanium, or a C-276 chrome/nickel alloy (e.g. Hastelloy® C-276). The tubular member preferably has relatively thin walls that can be effectively deflected by the piezoelectric ring. In one embodiment, the thickness of the walls of the tubular member is in the range of 0.1 mm to 0.5 mm, preferably about 0.25 mm. In one embodiment, the tubular member may have a shelf structure disposed around its inner surface to which the periphery of the vibratable plate may be bonded so that it extends across the internal lumen of the tubular member perpendicular to its central axis.

Various piezoelectric rings known in the art may be suitable for use as the annular vibration-inducing member of the present invention. In one embodiment, the piezoelectric ring may comprise any material exhibiting piezoelectric properties, for example, a piezoelectric ceramic material such as lead zirconate titanate (PZT) or lead metaniobate (PN) and may take the shape of a disc of substantially constant thickness with a central hole. Such piezoelectric rings are commercially available, e.g. from American Piezo Ceramics, Inc. (APC), Mackeyville, Pa., and from Morgan Electro Ceramics (MEC), Fairfield, N.J. The piezoelectric ring may be supplied with an alternating electric current at the selected frequency from a power source; for example, the piezoelectric ring may be electrically connected by wires to a controller that contains the electronics necessary to control the vibration of the piezoelectric ring.

In accordance with the invention, the tubular member is positioned within the center opening of the piezoelectric ring. When actuated by the alternating electrical fields from the controller, the piezoelectric ring expands and contracts in the radial direction against the walls of tubular member in the vicinity of the vibratable plate. This movement of the tubular member walls expands and contracts the periphery of the vibratable plate, thereby forcing the center of the vibratable plate to oscillate in the axial direction, i.e. to move up and down along the central axis of the tubular member. Although the piezoelectric ring may also vibrate in the axial direction and may create a transverse surface wave, only the radial vibration can transmitted to the vibratable plate by the tubular member. In this way, the superposition of conflicting vibration modes is eliminated and efficient translation of electrical energy to mechanical movement is accomplished. The practice of the present invention also allows the vibration system to be installed directly to a rigid body, such as the frame or housing of an aerosolizer, nebulizer or other device, without having the vibration transfer to the entire body. This is mainly because the ends of the tubular member do not vibrate and therefore may be used to install the vibration system to the rigid body.

The invention may be particularly useful when the tubular member is employed to hold an annular aperture plate or other structure having a plurality of apertures. When a liquid is applied to one side of the aperture plate through the tubular member and the piezoelectric ring is actuated, the aperture plate oscillates in a manner that causes liquid droplets to be ejected from the apertures. The resultant aerosol may then be dispensed out the open end of the tubular member.

A particularly useful type of aperture plate is one having tapered apertures that taper from the surface contacting the liquid to the surface where the droplets are ejected. Also, in some embodiments, the aperture plate may be domed shaped, although the invention is not limited to only such aperture plates. Preferred aperture plates may have a thickness in the range of 20 to 100 microns. Examples of piezoelectric materials and aperture plates that may be used with the invention are described in U.S. Pat. Nos. 6,235,177 and 5,758,637, incorporated herein by reference. In another embodiment, the piezoelectric ring may be vibrated at a frequency in the range from about 20 Khz to about 500 Khz, for example, about 128 Khz. In another preferred embodiment, the droplets may have a size suitable for use in pharmaceutics, for example, in the range from about 3 micrometers (μm) to about 6 μm, and the liquid may be aerosolized at a rate in the range from about 5-20 microliters/second.

Figure 2:
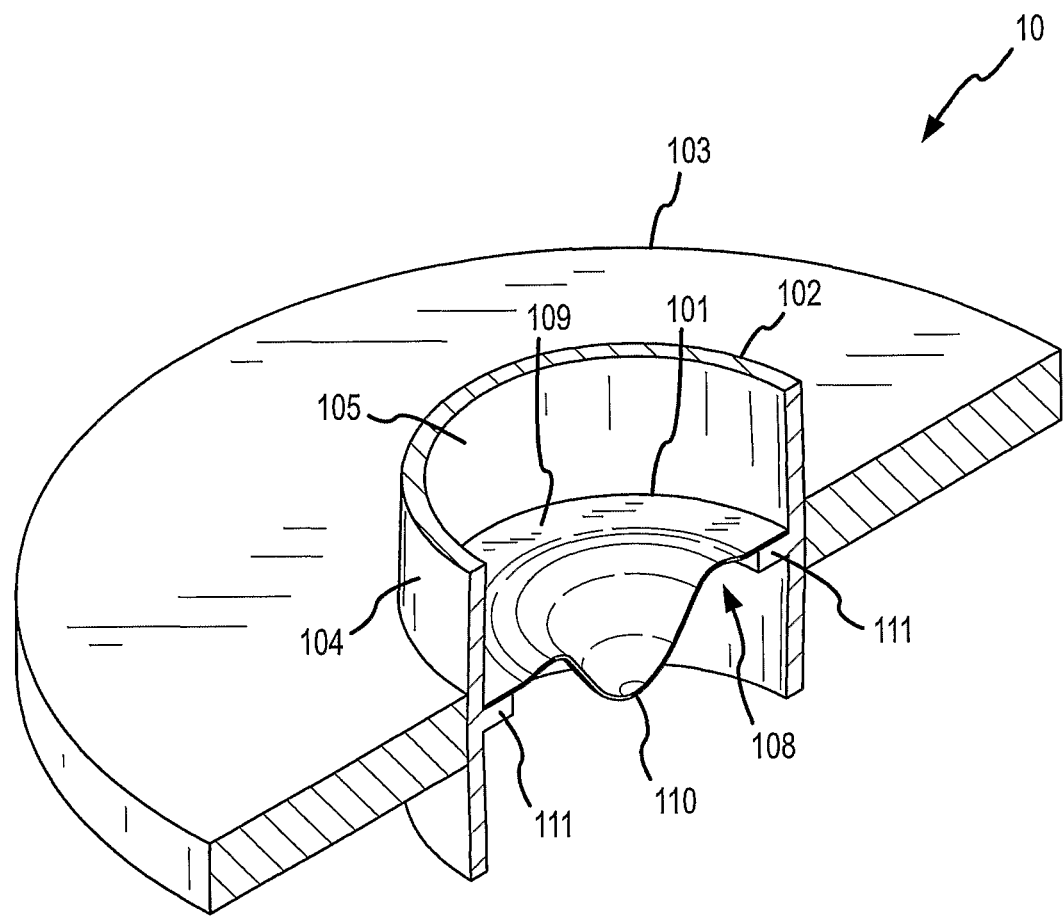
FIG. 2 is a partial cross-sectional view of the assembled vibration system of FIGS. 1a and 1b.

Referring now to FIGS. 1a, 1b and 2, one embodiment of the present invention will be described. Vibration system 10 comprises vibratable plate 101, tubular member 102 and piezoelectric ring 103. Tubular member 102 has an outer circumference 104 and an inner circumference 105, which together define a relatively thin cylindrical wall, preferably having a thickness in the range from about 0.1 mm to 0.5 mm. The hollow center (lumen) of tubular member 102 terminates in openings 106 and 107 at opposing ends thereof. Mounting structure 111 comprises a circular ridge that projects perpendicularly from inner circumference 105 into the lumen of tubular member 102 at a location, preferably a central location, between openings 106 and 107. Piezoelectric ring 103 comprises an annular disc of piezoelectric material having a center hole 108 with a circumference 112 approximately equal to the outer circumference 104 of tubular member 102. Vibratable plate 101 comprises circular outer flange 109 surrounding a thin circular vibratable center portion 110.

In one method of making vibration system 10, metallic tubular member 102 may first be provided with mounting structure 111 by bonding a ridge of metal around inner circumference 105 at a location equidistant from ends 106 and 107. Vibratable plate 101 may then be concentrically disposed within the lumen of tubular member 102 with the lower surface of circular flange 109 positioned over the upper surface of mounting structure 111 and with the outer periphery of vibratable plate 101 abutting inner circumference 105. Outer flange 109 of vibratable plate 101 may be secured onto mounting structure 111 using a suitable joining procedure, e.g. a metallurgical process such as brazing, welding, soldering or the like, or a chemical bonding process such as adhesive bonding.

In one preferred embodiment, a brazing ring of a suitable corrosion-resistant brazing filler material, e.g. a mixture of 70% gold and 30% copper, may be placed between the upper surface of mounting structure 111 and outer flange 109 of vibratable plate 101. The entire assembly of tubular member 102, vibratable plate 101 and brazing ring may be held in place by a weight placed on top of vibratable plate 101. The assembly may be placed in an oven and heated to a temperature sufficient to melt the brazing 1 and permanently join the surfaces together in a conventional brazing procedure. In another embodiment, vibratable plate 101 may be soldered onto mounting structure 111 using soldering materials, such as a tin/lead soldering material; however, this method may not be suitable if the assembly is to be exposed to acidic pharmaceutical preparations. In another embodiment, vibratable plate 101 may be secured onto mounting structure 111 by ultrasonic or laser welding.

Once vibratable plate 101 is secured across the lumen of tubular member 102, tubular member 102 may be positioned within center hole 108 of piezoelectric ring 103. In one embodiment, tubular member 102 may be placed in a fixture that holds tubular member 102 upright, and piezoelectric ring 103 may be slid lengthwise down tubular member 102 until piezoelectric ring 103 surrounds the outer circumference 104 at a location directly corresponding to the location of mounting structure 111 and vibratable plate 101 on inner circumference 105 of tubular member 102. Outer circumference 104 of tubular member 102 and circumference 112 of center hole 108 in piezoelectric ring 103 may then be bonded together, e.g. by depositing a suitable liquid adhesive around the juncture of circumference 104 and circumference 112 and curing the adhesive, e.g. with UV light. The adhesive used should be capable of efficiently transferring vibration from the piezoelectric ring 103 to tubular member 102. Although ideally the adhesive would have the modulus of elasticity ("Young's Modulus") of the piezoelectric ring, i.e. about 60 GPa (Giga Pascal), to achieve the ultimate transfer of vibration, this is not possible for any adhesive. Most structural adhesives (such as epoxy) have a modulus of elasticity of plastic material, which may be about 2 GPa, and should be suitable for the present invention if cured to approximately that stiffness. As examples of suitable adhesives, mention may be made of various epoxy and anaerobic adhesives, such as commercially available UV-cured epoxy adhesives sold under the trademark Loctite.

Figure 3A:
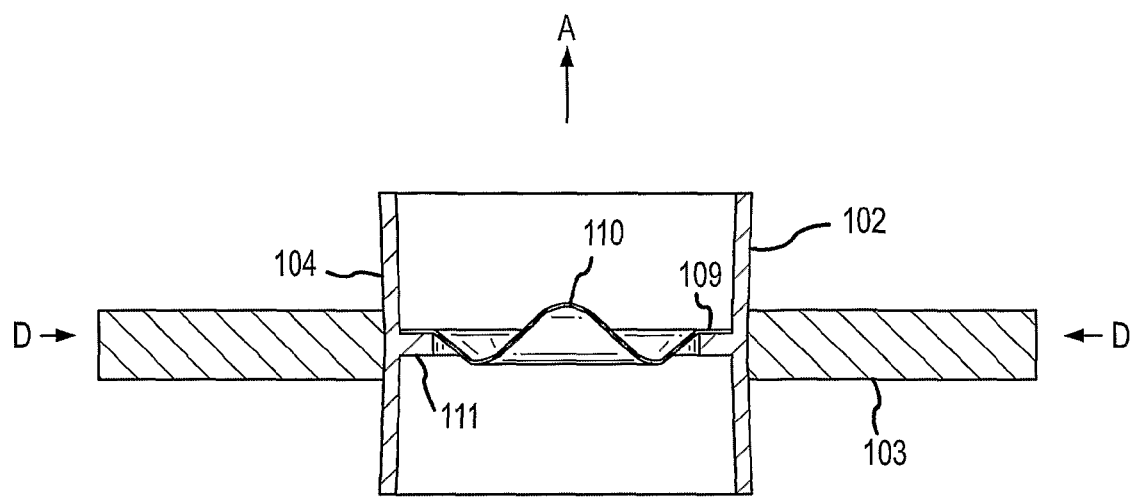
FIGS. 3a and 3b are cross-sectional side views of the vibration system of FIG. 2.
Figure 3B:
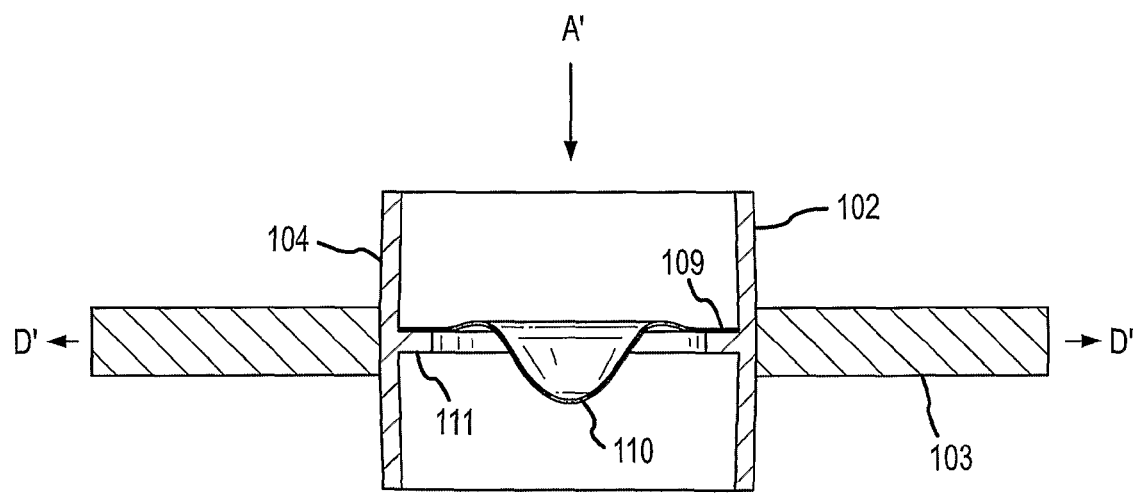

As previously described, piezoelectric ring 103 is configured to radially expand and contract when alternating electric fields are communicated to it via electric lines. For example, as illustrated in FIG. 3a, piezoelectric ring 103 contracts radially towards its center opening (direction D) when actuated by a first electric field. This radial contraction causes piezoelectric ring 103 to push inward along outer circumference 104 of tubular member 102 in the vicinity of mounting structure 111 and thereby pinch the wall of tubular member 102. The constriction of tubular member 102 causes flange 109 to also constrict radially and, as a result, the center portion 110 of vibratable plate 101 moves axially in direction A. When actuated by a second electric field, as shown in FIG. 3b, piezoelectric ring 103 expands radially away from its center opening (direction D'), thereby releasing the inward pressure along circumference 104 of tubular member 102. This release of pressure allows flange 109 to expand radially, which causes center portion 110 of aperture plate 101 to move axially in direction A' to its original position. Continually alternating the electric fields produces an oscillation (vibration) of center portion 110 between the positions shown in FIGS. 3a and 3b.

Figure 4A:
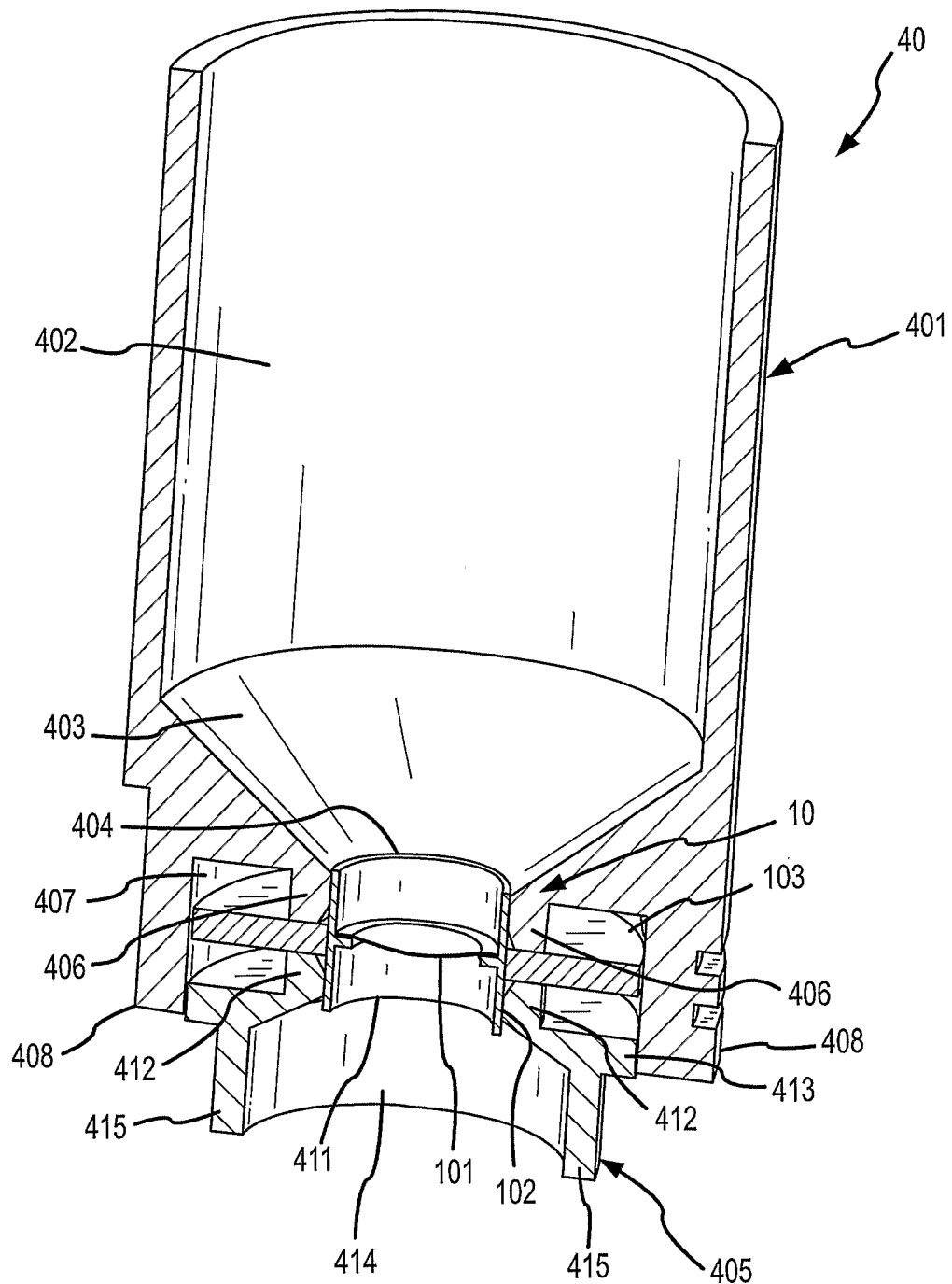
FIG. 4a is a cross-sectional side view of one embodiment of an aerosolizer according to the invention.
Figure 4B:
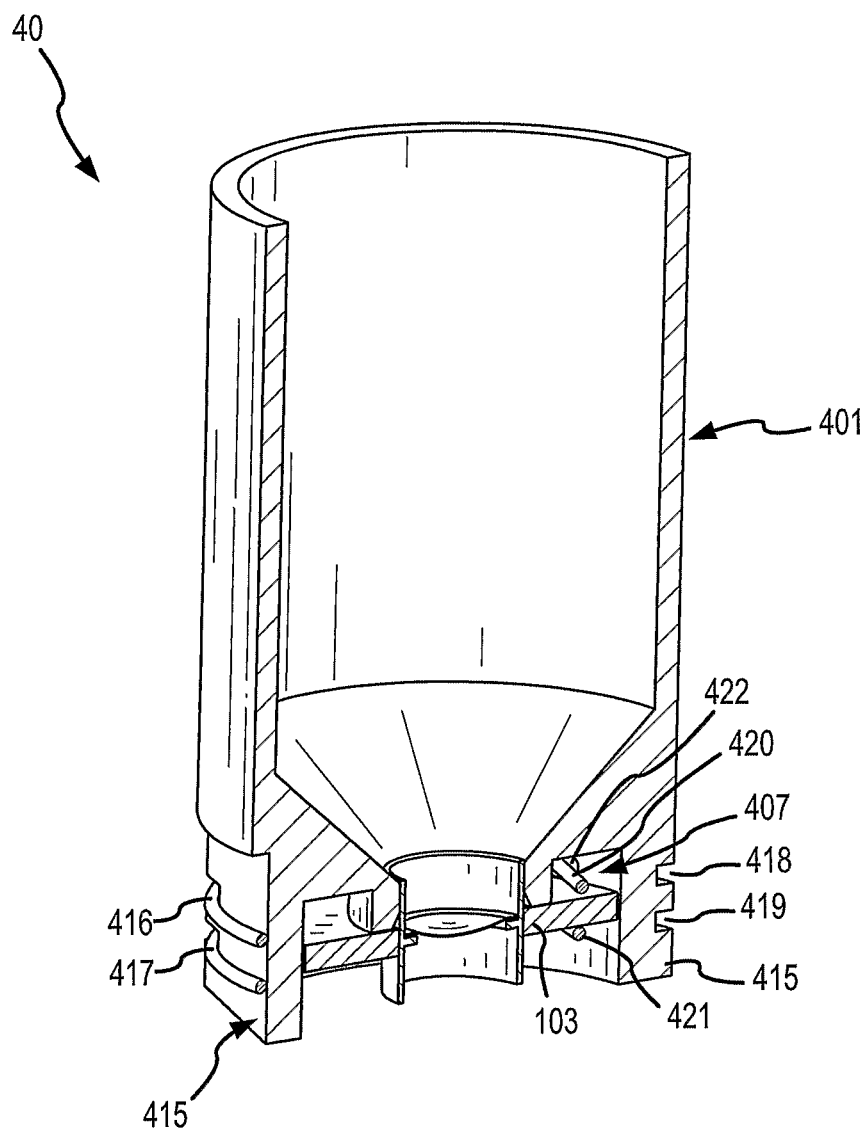
Figure 4C:
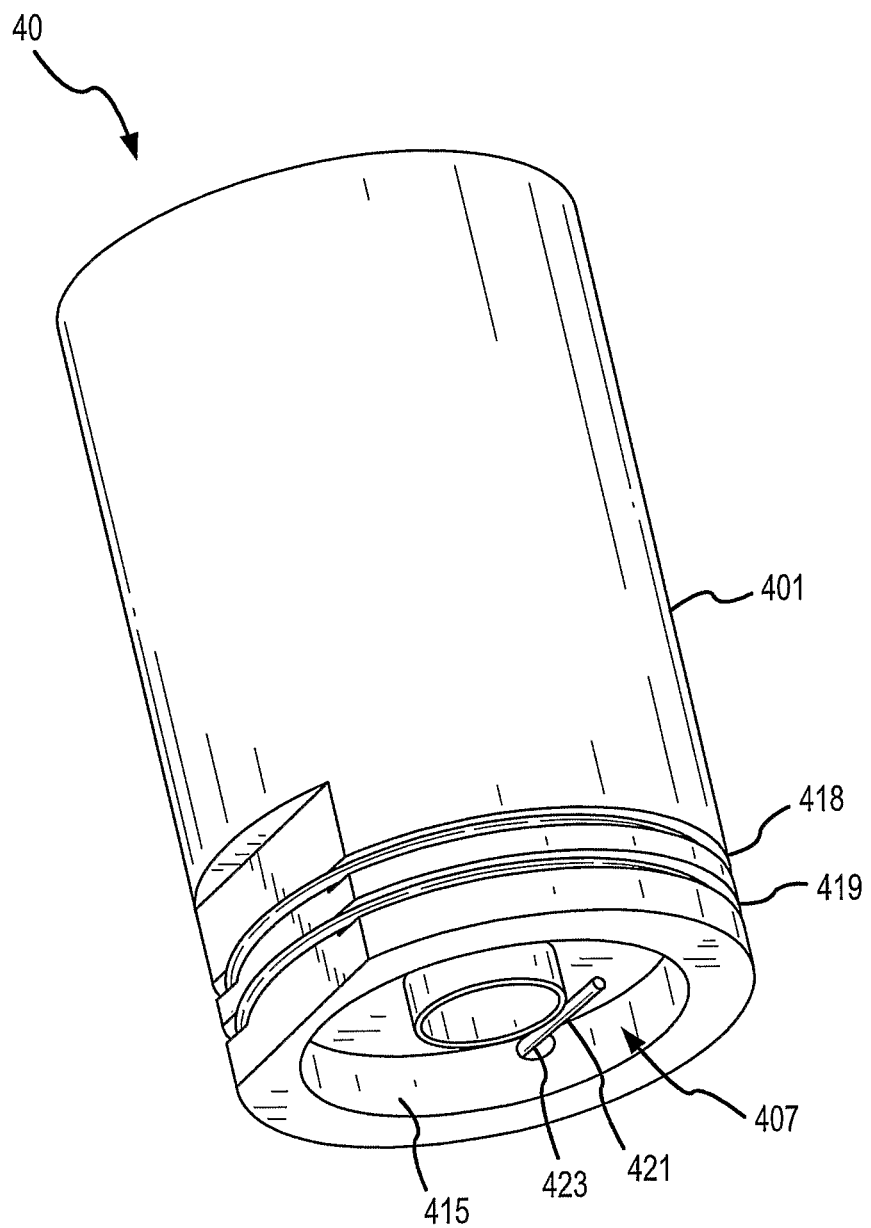

As previously mentioned, the vibration system of the present invention is particularly useful for aerosolizing liquids. FIGS. 4a, 4b and 4c illustrate an aerosolization system (referred to herein as "aerosolizer 40") in accordance with embodiments of the present invention. The same reference numbers are used in each of the Figures to refer to the same component. Referring now to FIG. 4a, aerosolizer 40 comprises upper housing 401, detachable lower housing 405 and vibration system 10 (e.g., see FIG. 2). Vibration system 10 comprises tubular member 102, piezoelectric ring 103 and aperture plate 101. Upper housing 401 comprises reservoir 402 configured to hold a volume of liquid, e.g. a liquid medicament, and a conical portion 403 at the lower end of reservoir 402 terminating in discharge tube 404 defined by cylindrical walls 406. Engagement tube 407 defined by cylindrical walls 408 of upper housing 401 is concentrically disposed around and completely encompasses discharge tube 404.

Vibration system 10 is adapted to be detachably engaged with upper housing 401, with the upper section of tubular member 102 of vibration system 10 (i.e., that section of tubular member 102 above piezoelectric ring 103) being configured to be press fit within discharge tube 404 and with piezoelectric ring 103 of vibration system 10 being configured to be press fit with engagement tube 407. When assembled, the upper section of tubular member 102 of piezoelectric ring 103 is fully encompassed by discharge tube 404 and the top surface of piezoelectric ring 103 abuts the lower end of discharge tube 404. This press fit mating of tubular member 102 and discharge tube 404 forms a liquid-tight seal that prevents liquid discharged from reservoir 402 into discharge tube 404 from coming in contact with piezoelectric ring 103.

Lower housing 405 comprises receiving tube 411 defined by cylindrical walls 412, annular flange 413 concentrically disposed around the base of receiving tube 411 and aerosol chamber 414 defined by cylindrical walls 415. Lower housing 405 may be adapted to be detachably engaged with vibration system 10 and upper housing 401, with the lower section of tubular member 102 of vibration system 10 (i.e., that section of tubular member 102 below piezoelectric ring 103) being configured to be press fit within receiving tube 411 and with annular flange 413 being configured to be press fit within engagement tube 407. When assembled, the lower section of tubular member 102 is fully encompassed by receiving tube 411 and forms a passageway directly into aerosol chamber 414. The bottom surface of piezoelectric ring 103 abuts the upper end of receiving tube 411 to securely hold vibration system 10 within engagement tube 407.

Referring now to FIGS. 4b and 4c, piezoelectric ring 103 may be supplied with an electric current by wires 416 and 417 from batteries or another power source (not shown). Each of wires 416 and 417 may be shaped in a "c-clip" arrangement and respectively nestled into grooves 418 and 419 cut around the periphery of walls 415 of upper housing 401. Terminal end 420 of wire 416 may enter engagement tube 407 through opening 422 in wall 415 and make electrical contact with the upper surface of piezoelectric ring 103. Terminal end 421 of wire 417 may enter engagement tube 407 through hole 423 in wall 415 of upper housing 401 and make electrical contact with the lower surface of piezoelectric ring 103.

Center portion 110 of aperture plate 101 may be dome-shaped in geometry, although other shapes may be used. Also, center portion 110 may include apertures that taper from the rear side (facing reservoir 402) to the front side. When aerosolizer 40 is placed in a generally vertical orientation, the liquid from reservoir 402 may be delivered to and rest on the rear side of center portion 110 by force of gravity. Piezoelectric ring 103 is configured to radially expand and contract when actuated by alternating electric fields supplied by wires 416 and 417. In so doing, the wall of tubular member 102 also constricts and expands. In this way, center portion 110 vibrates axially so as to eject liquid droplets from its front side and out the opening in aerosol chamber 414.

One advantage of using vibration system 10 is that aerosolizer 40 may be constructed so that vibration system 10 is removable from upper housing 401 and lower housing 405. In this way, vibration system 10 (which contains relatively expensive piezoelectric ring 103) may be reused in other applications. Upper housing 401 and lower housing 405, which may be able to be produced relatively inexpensively, may be discarded after use. Another advantage of using vibration system 10 is that the ends of tubular member 102 may be connected directly to rigid bodies, such as wall 406 of upper housing 401 and wall 412 of lower housing 405, without affecting the oscillating amplitude of aperture plate 110. This enables aerosolizer 40 to more efficiently produce liquid droplets.

Figure 4D:
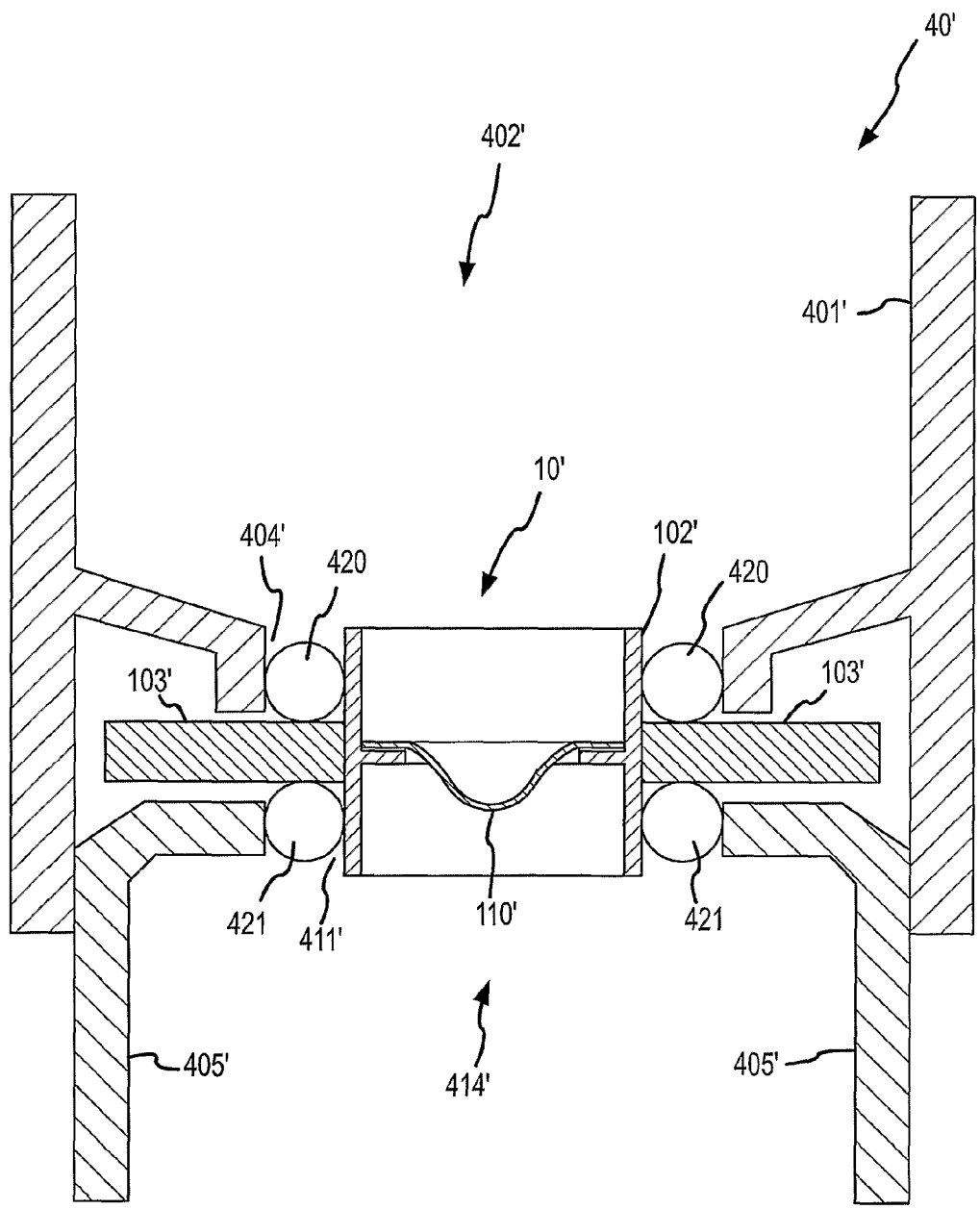
FIG. 4d is a cross-sectional side view of another embodiment of an aerosolizer according to the invention.

Referring now to FIG. 4d, aerosolizer 40' is similar to aerosolizer 40 and comprises upper housing 401' containing reservoir 402', detachable lower housing 405' containing aerosol chamber 414', and vibration system 10', which comprises tubular member 102', piezoelectric ring 103' and aperture plate center portion 110'. However, in aerosolizer 40', the upper section of tubular member 102' is not press fit into discharge tube 404' (as shown in FIG. 4a), but rather O-rings 420 may be positioned to fill a gap between the upper section of tubular member 102' and discharge tube 404' of housing 401'. In this way, a liquid-tight seal is formed that prevents liquid from reservoir 402' from contacting piezoelectric ring 103'. Similarly, O-rings 421 may be positioned to fill a gap between the lower section of tubular member 102' and receiving tube 411' of lower housing 405' to form a liquid-tight seal that prevents aerosol produced from aperture plate center portion 110' from contacting piezoelectric ring 103'. Accordingly, piezoelectric ring 103' may be protected from contamination that may prevent it from being re-usable after removal from aerosolizer 40', without the tight dimensions required for a press fit, as described in connection with aerosolizer 40. Since O-rings 420 and 421 are positioned on both top and bottom surfaces of piezoelectric ring 103' and serve to suspend piezoelectric ring 103' from direct contact with upper housing 401' and lower housing 405', O-rings 420 and 421 may also have a dampening effect that reduces the undesirable transfer of vibration from piezoelectric ring 103' to upper housing 401' and lower housing 405'.

Figure 5A:
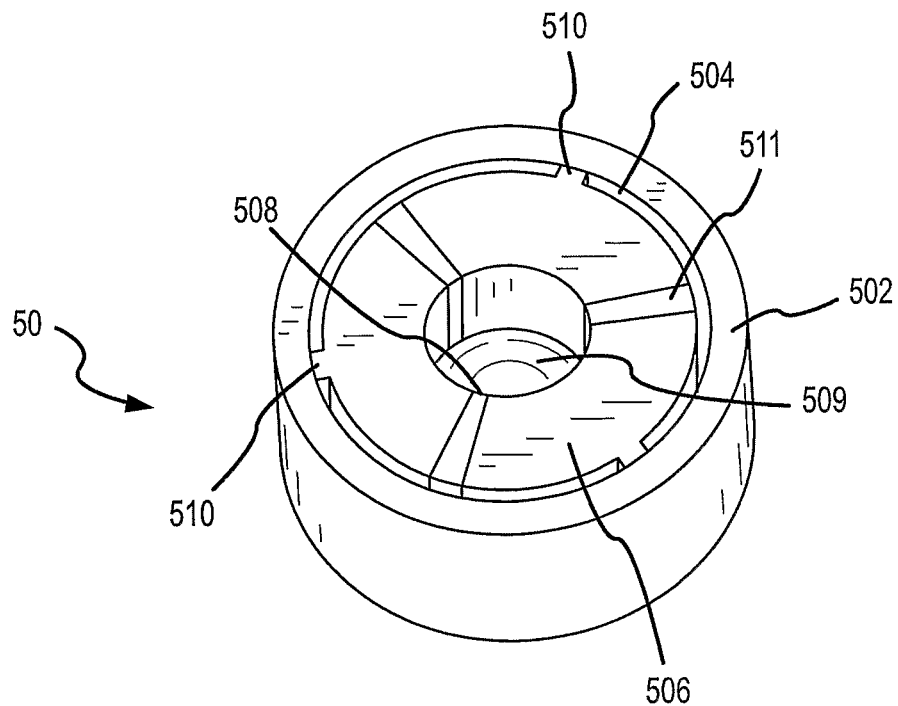
FIG. 5a is a perspective view of another embodiment of a vibration system according to the invention.
Figure 5B:
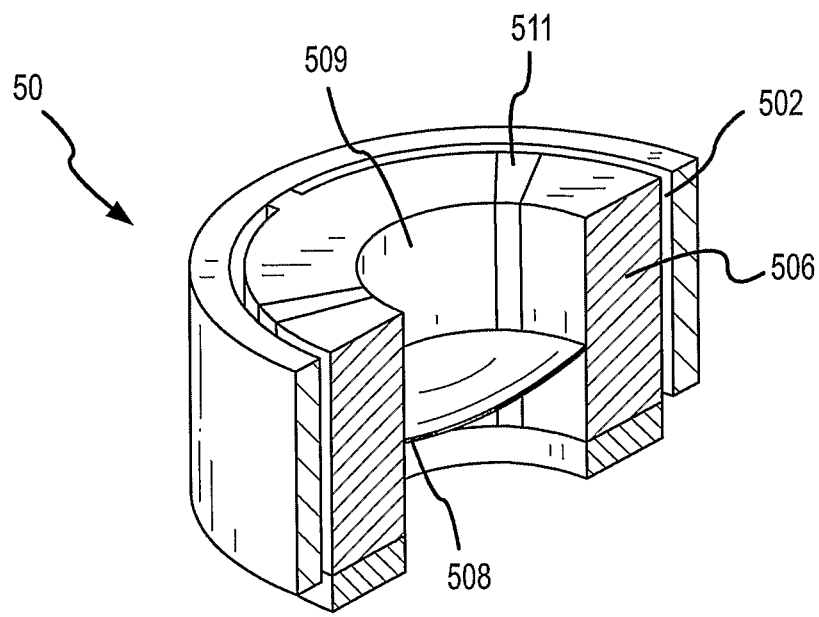
FIG. 5b is a partial cross-sectional view of the vibration system shown in FIG. 5a FIG. 6 is a perspective view of another embodiment of a vibration system according to the invention.

Referring now to FIGS. 5a and 5b, another embodiment of the present invention will be described. Vibration system 50 comprises a piezoelectric ring 502 having a central opening 504. Piezoelectric ring 502 may be constructed of a piezoelectric material that radially expands and contracts when actuated, as previously discussed. Tubular member 506 is disposed within opening 504 and is adapted to hold aperture plate 508 within its internal lumen 509 using any of the techniques described herein. Tubular member 506 may be constructed of a rigid material, such as a hard plastic, metal, ceramic or the like. Tubular member 506 may optionally include projections 510 to provide a good mechanical contact with piezoelectric ring 502. As an alternative, tubular member 506 may be tapered to assure a good mechanical contact.

Tubular member 506 may include one or more resilient segments 511 radially extending from locations on its inner circumference to corresponding locations on its outer circumference. These segments may be constructed from an elastomeric material and positioned in various locations. Resilient segments 511 permit tubular member 506 to be constructed of a rigid material (for securely holding aperture plate 508) while also permitting tubular member 506 to radially expand and contract with piezoelectric ring 502. More specifically, as tubular member 506 is constricted by piezoelectric ring 502, resilient segments 511 compress to reduce the diameter of lumen 509. When piezoelectric ring 502 radially expands, resilient segments 511 expand to increase the diameter of lumen 509. Hence, the amount of expansion and contraction may be varied based in part on the size, number and types of resilient materials used.

Conveniently, vibration system 50 may be coupled to a reservoir of an aerosolizer (not shown) to permit a liquid to be supplied to aperture plate 508. Also, other liquid delivery systems could be used as well, such as wicking systems, and the like. Alternatively, vibration system 50 may be incorporated into other systems, such as nebulizers, ventilators and the like.

Figure 6:
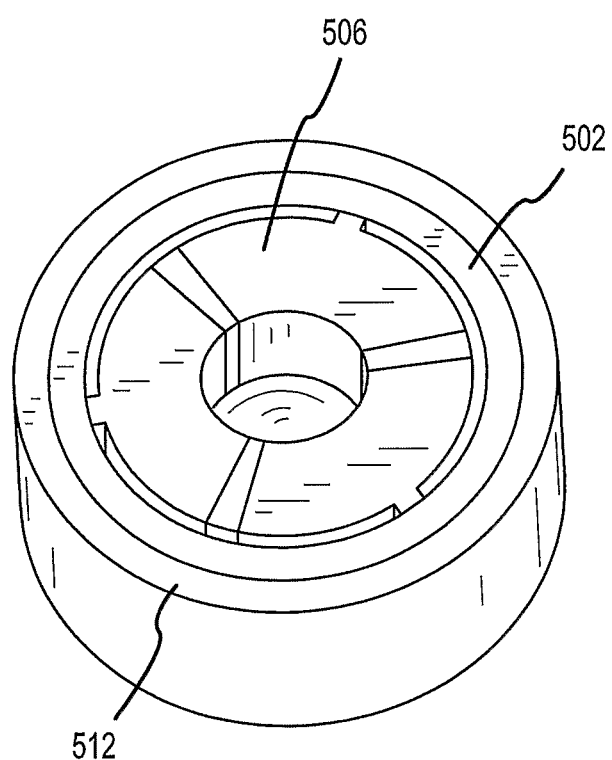

FIG. 6 illustrates vibration system 50, as shown in FIGS. 5a and 5b, with an outer ring 512 disposed about the outer circumference of piezoelectric ring 502, which in turn in disposed around tubular member 506. Ring 512 may be employed to adjust the operating frequency of piezoelectric ring 502. In many applications, it is desirable to operate piezoelectric ring 502 at a frequency of about 130 Khz, which is the approximate resonance frequency of the aperture plate. When piezoelectric ring 502 is constructed from a piezoceramic material, its frequency is inversely proportional to its diameter where:

$$f=(1/2\pi i r)X\sqrt{(E/p)}$$

Hence, if the diameter of the piezoelectric ring 502 is made larger to reduce the frequency of the piezoelectric ring, the piezoelectric ring 502 may be too large for certain applications. A low operating frequency of piezoelectric ring 502 may result because the piezoelectric material is "soft" and heavy. To increase the frequency without increasing the diameter, outer ring 512 (which may be constructed of a stiff and lightweight material, such as silicon nitride) may be added. The combination of ring 512 and piezoelectric ring 502 serves to increase the frequency to the desired range.

Figure 7A:
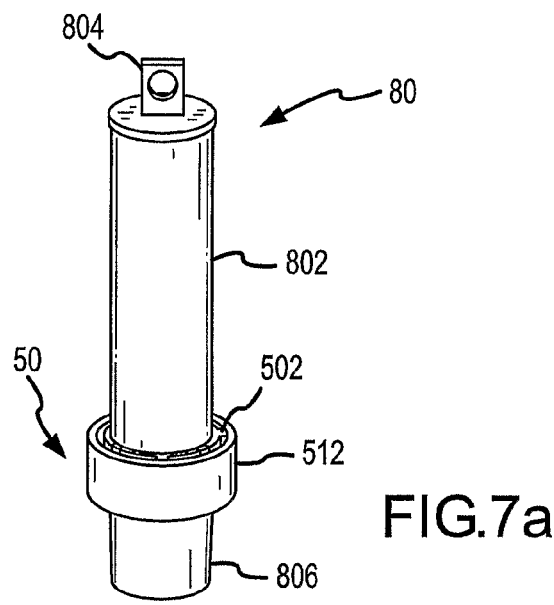
FIG. 7a is a perspective view of another embodiment of an aerosolizer according to the invention.
Figure 7B:
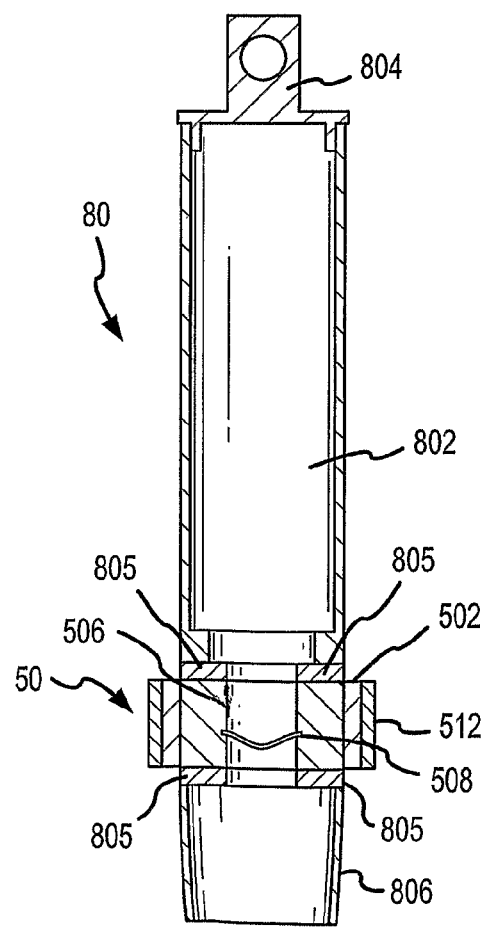

Referring to FIGS. 7a and 7b, an embodiment of an aerosolization system in accordance with the present invention will be described. System 80 includes an aerosolizer that, for convenience of discussion, includes vibration system 50 having ring 512, as shown in FIG. 6, although it will be appreciated that other vibration systems of the invention could be used as well. Coupled to (or integrally formed with) tubular member 506 of vibration system 50 is a container 802 for holding a liquid. Conveniently, a lid 804 may be provided to close container 802 after filling it with a liquid. Also coupled to tubular member 506 is an outlet 806 through which an aerosol produced by aperture plate 508 may be dispensed. O-rings or gasket seals 805 may be disposed between container 802 and vibration system 50, and between vibration system 50 and outlet 806 to provide adequate sealing and cushioning between the components.

One particular feature of aerosolization system 80 is that piezoelectric ring 502 has a large enough inner diameter that it may be slid over outlet 806 and container 802. In this way, system 80 may be easily assembled and disassembled to remove piezoelectric ring 502. Further, piezoelectric ring 502 does not come into contact with any liquids and therefore may be reused with another aerosolization system. Further, container 802, tubular member 506 and aperture plate 508 may be constructed to be relatively inexpensive so that they may be disposed of following use. Also, system 80 may easily be incorporated into other systems, such as hand-held nebulizers, ventilators and the like.

In operation, container 802 is filled with a liquid and lid 804 is put in place. Piezoelectric ring 502 is slid over container 802 and placed over tubular member 506. An electric current is supplied to piezoelectric ring 502 to cause it to expand and contract. In so doing, liquid that is in contact with aperture plate 508 is ejected as liquid droplets into outlet 806. Following use, container 802 may be refilled, or may be discarded while saving piezoelectric ring 502.

Figure 8:
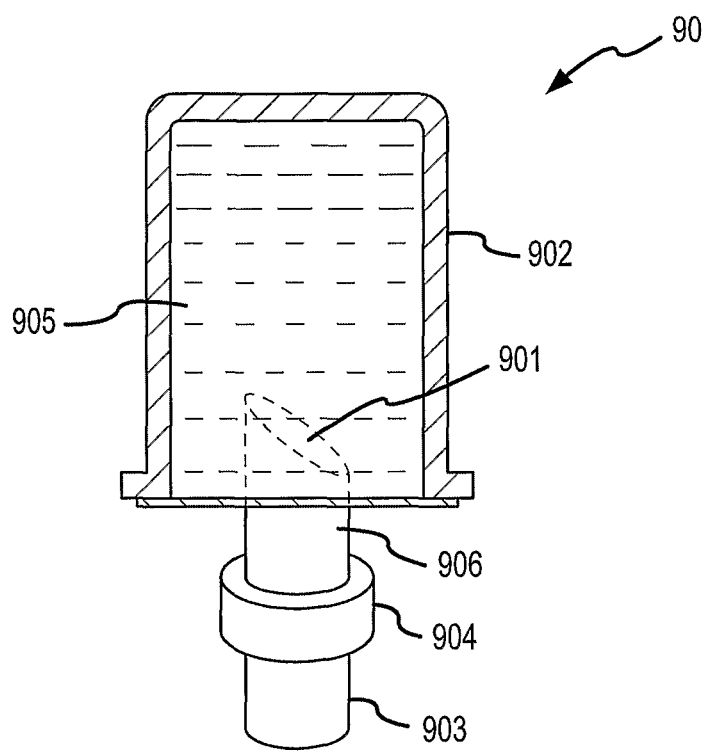
FIG. 8 is a cross-sectional side view of another embodiment of an aerosolizer system according to the invention.

FIG. 8 illustrates another embodiment of the invention wherein aerosolization system 90 includes tubular member 906 comprising a sharpened end 901 and a discharge end 903. As previously described, tubular member 906 also contains an aperture plate (not shown) across its internal lumen. Piezoelectric ring 904 is disposed around tubular member 906. When aerosolization system 90 is not in use, sharpened end 901 may have a cover (not shown) that protects it from damage and contamination. When ready for use, the cover may be removed and sharpened end 901 may be inserted through the membrane top of a vial 902, which contains liquid 905 to be aerosolized. Liquid 905 is then delivered through sharpened end 901 and the lumen of tubular member 906 to the aperture plate contained therein. Piezoelectric ring 904 may be actuated to vibrate the aperture plate and thereby aerosolize liquid 905 in the manner previously described. The resultant aerosol is then dispensed through discharge end 903. After use, vial 902 may be removed from sharpened end 901 and discarded, piezoelectric ring 904 may be removed from the assembly for re-use, and the remaining assembly may be discarded.

As previously mentioned, the aerosolizers described herein may be incorporated into other systems. Example of ventilator systems are described, for example, in co-pending U.S. patent application Ser. No. 10/828,765, filed Apr. 20, 2004, the complete disclosure of which is herein incorporated by reference. The system described therein is particularly useful in neo-natal and infant continuous positive pressure airway pressure (CPAP) therapies. Accordingly, an aerosolizer of the present invention may be coupled to such a ventilator or CPAP circuit to supply aerosolized medicament to a patient's respiratory system, e.g. through a patient interface device. When the treatment is finished, the aerosolizer, or certain components thereof, may be removed and re-used, while other components of the system may be discarded.

As another example, the aerosolizer of the present invention may be incorporated in a nebulizer such as described in co-pending U.S. patent application Ser. No. 10/833,932, filed Apr. 27, 2004, the complete disclosure of which is herein incorporated by reference. The nebulizer comprises a main housing coupled to an aerosolizer housing, which may comprise an aerosolization system such as previously described in connection with aerosolizer 40 shown in FIGS. 4a, 4b and 4c, including a reservoir for holding a liquid medicament that is to be aerosolized and a vibration system according to the present invention having an aperture plate with a plurality of tapered apertures extending between a first surface and a second surface, as described in U.S. Pat. Nos. 5,164,740, 5,586,550, 5,758,637, and 6,085,740, the entire contents of which are incorporated herein by this reference. The nebulizer may also have a mouthpiece coupled to the main housing. At least a portion of the tubular member of the vibration system of the present invention may be disposed in the housing so that liquid droplets are ejected through the mouthpiece to permit a patient to inhale the aerosolized medicament. The apertures in the aperture plate may be sized to produce an aerosol in which about 70% or more of the droplets by weight have a size in the range from about 1 to about 5 micrometers. Following use, the aerosol housing may be removed from the main housing. The liquid may be refilled, or one or more components may be replaced. For example, the vibration system may be removed and reused with another nebulizer.

One embodiment of the present invention provides a method of treating a patient that exhibits one or more symptoms of infection or other respiratory disease or disorder. The method generally comprises the steps of: providing a vibration system comprising a circular vibratable aperture plate having an outer circumference, a tubular member concentrically disposed about the outer circumference of the vibratable plate, wherein the tubular member has an outer circumference, and an annular vibration-inducing member concentrically disposed about the outer circumference of the tubular member, wherein the vibration-inducing member is radially expandable and contractable to cause the aperture plate to vibrate in the axial direction; supplying a liquid medicament to the vibration system; actuating the vibration-inducing member to vibrate the aperture plate and aerosolize the medicament; and supplying the aerosol to the patient's respiratory system.

An aerosol generator in accordance with the present invention has the ability to produce a high flow of aerosol relative to the power input. For example, when standard saline solution (2% NaCl) is used, the flow rate of aerosol having a volumetric median diameter (VMD) of 4 microns may be 15 microliters/sec and the power consumption of the generator may be 3 watts.

The invention has now been described in detail for purposes of clarity and understanding. However, it will be appreciated that certain changes and modifications may be practiced within the scope of the appended claims.

I claim:

1. A vibration system comprising:
    a circular vibratable plate having an outer circumference;
    a tubular member concentrically disposed about and in contact with the outer circumference of the plate, the tubular member aligning the circular vibratable plate, wherein the tubular member has an outer circumference;
    a mounting structure disposed inside the tubular member, the mounting structure supporting the circular vibratable plate; and
    an annular vibration-inducing member concentrically disposed about the outer circumference of the tubular member, wherein the vibration-inducing member is radially expandable and contractable against the tubular member to cause the plate to vibrate in the axial direction.

2. A system as in claim 1, wherein the vibration-inducing member comprises a piezoelectric ring.

3. A system as in claim 2, wherein the tubular member includes at least one resilient segment disposed therein.

4. A system as in claim 3, wherein a ring is disposed around the outer circumference of the piezoelectric ring to adjust the operating frequency of the piezoelectric ring.

5. A system as in claim 1, wherein the plate includes a plurality of tapered apertures.

6. A system as in claim 5, wherein the plate has a thickness in the range from about 20 microns to about 100 microns.

7. A system as in claim 5, wherein the plate is dome-shaped.

8. A system as in claim 5, further comprising a reservoir of liquid which is adapted to supply the liquid to the plate.

9. A system as in claim 5, wherein the tubular member includes a sharpened end adapted to extract liquid from a vial of liquid by piercing a membrane covering an opening in said vial.

10. A system as in claim 1, wherein the tubular member has a wall thickness in the range from about 0.1 mm to about 0.5 mm.

11. A system as in claim 1, further comprising a controller for controlling the radial expansion and contraction of the vibration-inducing member and wires connecting the controller to the vibration-inducing member.

12. A system as in claim 1 wherein the vibration-inducing member is removable from the tubular member.

13. A vibration system comprising:
    a vibratable plate having an outer circumference;
    a support member surrounding and in contact with the outer circumference of the vibratable plate, the support member aligning the vibratable plate; and
    a vibration-inducing member that is a piezoelectric ring surrounding the support member, wherein the vibration-inducing member is configured to radially expand and contract against the support member so as to produce axial vibration of the vibratable plate.

14. A vibration system as in claim 13 wherein the vibratable plate is circular, the support member has a circular cross-section into which the circular vibratable plate is disposed, and the vibration-inducing member is an annular disc having a central opening into which the support member is disposed.

15. A vibration system as in claim 14 wherein the support member comprises a thin-walled tubular member.

16. The vibration system of claim 13 wherein the vibration inducing member is in co-planar alignment with a periphery of the vibratable plate.

17. An aerosol generating system, comprising:
    a piezoelectric ring having a center hole with an inner circumference adapted to expand and contract radially when electrically activated;
    at least one electrical connection to said piezoelectric ring for electrical actuation thereof a tubular member disposed within the center hole of the piezoelectric ring, said tubular member having an outer circumference in contact with the inner circumference of said center hole and a cylindrical wall defining an internal lumen extending the length of the tubular member;
    a circular vibratable aperture plate adapted to aerosolize a liquid upon axial vibration thereof;
    wherein the aperture plate is disposed across the internal lumen of the tubular member and in contact with the inner circumference of the lumen at a location coinciding with the inner circumference of the center hole of the piezo electric ring, the tubular member including a mounting structure for supporting the aperture plate; and
    a reservoir of liquid coupled to the tubular member so as to supply liquid to the vibratable aperture plate, whereby radial expansion and contraction of the piezo electric ring against the wall of the tubular member causes the aperture plate to vibrate in the axial direction and aerosolize the liquid.

18. An aerosol generating system as in claim 17 wherein the vibratable plate is domed-shaped and has a plurality of tapered apertures.

19. An aerosol generating system as in claim 17 wherein the piezoelectric ring comprises piezoelectric ceramic material.

20. An aerosol generating system as in claim 17 further comprising a circuit of a ventilator system operably connected to the tubular member so as to dispense aerosol generated by said vibratable aperture plate into said circuit.

21. An aerosol generating system as in claim 17 wherein said piezoelectric ring, said tubular member, said vibratable aperture plate and said reservoir are disposed within the housing of a nebulizer having a mouthpiece.

22. A vibration system comprising:
    a tubular alignment member having a cylindrical wall defining a longitudinal lumen;
    a vibratable plate secured to a mounting structure of the cylindrical wall and disposed across the lumen with the outer circumference of the vibratable plate being surrounded by and in contact with the cylindrical wall; and
    means for imparting radial vibration to the cylindrical wall of the tubular member so as to produce axial vibration in the vibratable plate.

23. A vibration system as in claim 22 wherein the vibratable plate is an aperture plate having a rear surface in contact with a liquid and a front surface opposed thereto, wherein liquid droplets are ejected from the front surface to form an aerosol upon said axial vibration of the aperture plate.

24. An aerosol generator device comprising:
- a vibratable plate,
- an alignment member for receiving and holding the vibratable plate in a predetermined position, wherein the alignment member surrounds an is in contact with an outer circumference of the vibratable plate, and
- a vibration-inducing member in communication with the alignment member, wherein the vibration inducing member is a piezoelectric ring having a center hole with an inner circumference, and wherein the piezoelectric ring surrounds the alignment member with the inner circumference of the piezoelectric ring in contact with the alignment member.

25. The device of claim 24, wherein a portion of the device is disposable.

26. A method for vibrating a plate, comprising:
- providing a plate having an outer circumference and a tubular member disposed about and in contact with the outer circumference of the plate, said tubular member having an outer circumference;
- aligning the plate using the tubular member;
- providing a piezoelectric ring concentrically positioned about the outer circumference of the tubular member at a location coinciding with the outer circumference of the plate; and
- radially expanding and contracting the piezoelectric ring against the tubular member so as to cause the plate to vibrate in the axial direction.

27. A method as in claim 26, wherein the plate includes a plurality of apertures, and further comprising supplying a liquid to the plate to aerosolize the liquid as liquid droplets.

28. A method as in claim 27, wherein the droplets have a size in the range from about 3 micrometers to 6 micrometers, and wherein the liquid is aerosolized at a rate of about 5 microliters/second to about 20 microliters/second.

29. A method as in claim 27, further comprising coupling a reservoir to the tubular member to supply the liquid to the plate.

30. A method as in claim 26, wherein the piezoelectric ring is vibrated at a frequency in the range from about 20 Khz to about 500 Khz.

31. A method of making a vibration system comprising:
- providing a tubular member having a lengthwise lumen;
- aligning and securing a circular vibratable plate within the lumen so that the plate is perpendicular to and covers the lumen of the tubular member, and is in contact with an inner circumference of the lumen;
- positioning the tubular member within the center hole of a piezoelectric ring so that the vibratable plate within the lumen of the tubular member is surrounded by the piezoelectric ring in contact with the outer circumference of the tubular member; and
- securing the piezoelectric ring to the tubular member.

32. A method of making a vibration system as in claim 31, further comprising the steps of:
- bonding a ridge around the inner circumference of the tubular member;
- positioning the vibratable plate on the ridge; and
- brazing or welding the vibratable plate to the ridge.

33. A method of making a vibration system as in claim 31 wherein the piezoelectric ring is bonded to the tubular member with an adhesive capable of efficiently transferring vibration from piezoelectric ring to the tubular member.

34. A method of treating a patient comprising:
- providing a vibration system comprising a vibratable aperture plate having an outer circumference, providing a tubular alignment member concentrically disposed about and in contact with the outer circumference of the vibratable plate, the tubular alignment member having a mounting structure for holding the vibratable plate, wherein the tubular alignment member has an outer circumference, and a piezoelectric ring concentrically disposed about the outer circumference of the tubular alignment member at a location coinciding with the outer circumference of the aperture plate, supplying a liquid medicament to the aperture plate;
- electrically actuating the piezoelectric ring to radially expand and contract the wall of the tubular alignment member around the outer circumference of the aperture plate, thereby causing the aperture plate to vibrate in the axial direction and aerosolize the medicament; and
- supplying the aerosol to the patient's respiratory system.

35. A method of treating a patient as in claim 34 wherein the aerosol is supplied to the patient's respiratory system through the circuit of a ventilator or CPAP system.

36. A method of treating a patient as in claim 34 wherein the aerosol is supplied to the patient's respiratory system through a nebulizer having a mouthpiece.

37. A method of vibrating a plate comprising the steps of:
- inserting a vibratable plate having an outer circumference into a support structure that surrounds the plate;
- aligning the vibratable plate using the support structure, the support structure being in contact with the outer circumference of the vibratable plate;
- surrounding the support structure including vibratable plate with a vibration-inducing member that is configured to expand and contract radially; and
- actuating the vibration-inducing member to produce radial expansion and contraction against the support member to cause axial vibration of the vibratable plate;
- wherein the support structure filters out vibration other than axial vibration.

38. A method of making a vibration system comprising:
- aligning a vibratable plate within a support member that surrounds the vibratable plate; and
- placing around the support member a vibration-inducing member configured to radially expand and contract against the support member to produce axial vibration of the vibratable plate; wherein the support member is tubular and the aligning includes placing the vibratable plate within the tubular support member and in contact with a mounting structure of the tubular support member such that an outer circumference of the vibratable plate is in contact with an inner circumference of the tubular support member.

* * * * *